US008617562B2

(12) United States Patent
Tsunoda et al.

(10) Patent No.: US 8,617,562 B2
(45) Date of Patent: Dec. 31, 2013

(54) FOXM1 PEPTIDES AND IMMUNOGENIC COMPOSITIONS CONTAINING THEM

(75) Inventors: Takuya Tsunoda, Kanagawa (JP); Ryuji Ohsawa, Kanagawa (JP); Sachiko Yoshimura, Kanagawa (JP); Tomohisa Watanabe, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 0 days.

(21) Appl. No.: 13/202,078

(22) PCT Filed: Feb. 17, 2010

(86) PCT No.: PCT/JP2010/001005
§ 371 (c)(1),
(2), (4) Date: Feb. 3, 2012

(87) PCT Pub. No.: WO2010/095428
PCT Pub. Date: Aug. 26, 2010

(65) Prior Publication Data
US 2012/0156231 A1    Jun. 21, 2012

Related U.S. Application Data

(60) Provisional application No. 61/153,408, filed on Feb. 18, 2009.

(51) Int. Cl.
*A61K 39/00* (2006.01)
*C12P 21/08* (2006.01)

(52) U.S. Cl.
USPC ............... 424/185.1; 435/70.1; 435/70.4

(58) Field of Classification Search
None
See application file for complete search history.

(56) References Cited

U.S. PATENT DOCUMENTS

| | | | |
|---|---|---|---|
| 5,861,278 | A | 1/1999 | Wong et al. |
| 6,747,137 | B1 | 6/2004 | Weinstock et al. |
| 7,531,300 | B2 | 5/2009 | Nakamura et al. |
| 7,700,573 | B2 * | 4/2010 | Nakamura et al. .......... 514/44 R |
| 2005/0260639 | A1 | 11/2005 | Nakamura et al. |
| 2006/0014686 | A1 | 1/2006 | Wonsey et al. |
| 2006/0024692 | A1 | 2/2006 | Nakamura et al. |
| 2007/0083334 | A1 | 4/2007 | Mintz et al. |
| 2008/0050378 | A1 | 2/2008 | Nakamura et al. |
| 2009/0162361 | A1 | 6/2009 | Nakamura et al. |
| 2009/0175844 | A1 | 7/2009 | Nakamura et al. |
| 2009/0208514 | A1 | 8/2009 | Nakamura et al. |
| 2009/0286856 | A1 | 11/2009 | Nakamura et al. |
| 2009/0311685 | A1 | 12/2009 | Nakamura et al. |
| 2009/0317392 | A1 | 12/2009 | Nakamura et al. |
| 2010/0173317 | A1 | 7/2010 | Nakamura et al. |
| 2011/0152199 | A1 | 6/2011 | Nishimura et al. |
| 2011/0195081 | A1 | 8/2011 | Nishimura et al. |
| 2011/0223687 | A1 | 9/2011 | Nakamura et al. |
| 2012/0010090 | A1 | 1/2012 | Nakamura et al. |
| 2012/0014996 | A1 | 1/2012 | Nakamura et al. |
| 2012/0021946 | A1 | 1/2012 | Nakamura et al. |
| 2012/0093845 | A1 | 4/2012 | Tsunoda et al. |

FOREIGN PATENT DOCUMENTS

| | | |
|---|---|---|
| EP | 0846761 A1 | 6/1998 |
| EP | 1462456 A1 | 9/2004 |
| EP | 1806413 A1 | 7/2007 |
| EP | 2189471 A1 | 5/2010 |
| JP | 11-510507 A | 9/1999 |
| JP | 2005-518192 A | 6/2005 |
| JP | 2006-141208 A | 6/2006 |
| JP | 2007-530006 A | 11/2007 |
| WO | 97/05900 A1 | 2/1997 |
| WO | 02/099076 A2 | 12/2002 |
| WO | 03/037060 A2 | 5/2003 |
| WO | 03/050140 A1 | 6/2003 |
| WO | 2004/019761 A2 | 3/2004 |
| WO | 2004/031412 A2 | 4/2004 |
| WO | 2004/031413 A2 | 4/2004 |
| WO | 2004/100977 A1 | 11/2004 |
| WO | 2005/028676 A2 | 3/2005 |
| WO | 2005/058937 A2 | 6/2005 |
| WO | 2005/090603 A2 | 9/2005 |
| WO | 2005/090991 A1 | 9/2005 |
| WO | 2006/085684 A2 | 8/2006 |
| WO | 2007/013665 A2 | 2/2007 |
| WO | 2007/013671 A2 | 2/2007 |
| WO | 2007/123247 A1 | 11/2007 |
| WO | 2009/025117 A1 | 2/2009 |
| WO | 2009/025196 A1 | 2/2009 |

OTHER PUBLICATIONS

Belli, et al. "Vaccination of Metastatic Melanoma Patients with Autologous Tumor-Derived Heat Shock Protein gp96-Peptide complexes: Clinical and Immunologic Findings," *J Clin Oncol.*, vol. 20(20), pp. 4169-4180 (Oct. 15, 2002).

Boon, "Tumor Antigens Recognized by Cytolytic T Lymphocytes: Present Perspectives for Specific Immunotherapy," *Int J Cancer*, vol. 54(2), pp. 177-180 (May 8, 1993).

Boon, et al., "Human Tumor Antigens Recognized by T Lymphocytes," *J Exp Med.*, vol. 183(3), pp. 725-729 (Mar. 1, 1996).

Butterfield, et al., "Generation of Human T-cell responses to an HLA-2.1 restricted Peptide Epitope Derived from α-Fetoprotein," *Cancer Res.*, vol. 59(13), pp. 3134-3142 (Jul. 1, 1999).

(Continued)

*Primary Examiner* — Elly-Gerald Stoica
(74) *Attorney, Agent, or Firm* — Kilpatrick Townsend & Stockton LLP

(57) ABSTRACT

The present invention provides isolated peptides having the amino acid sequence of SEQ ID NO: 34 or fragments thereof, which bind to HLA antigen and induce cytotoxic T lymphocyte (CTL). The present invention further provides peptides which include one, two, or several amino acid insertions, substitution or addition to the aforementioned peptides or fragments, but still have the cytotoxic T cell inducibility. Further provided are nucleic acids encoding any of these aforementioned peptides as well as pharmaceutical substances or compositions including any of the aforementioned peptides or nucleic acids. The peptides, nucleic acids, pharmaceutical substances or compositions of the present invention may be used for treating cancer or tumor.

7 Claims, 4 Drawing Sheets

(56) References Cited

OTHER PUBLICATIONS

Coulie, et al., "Cytolytic T-cell Responses of cancer patients vaccinated with a MAGE antigen," *Immunol Rev.*, vol. 188(1), pp. 33-42 (Oct. 2002).

Dionne, et al., "Functional characterization of CTL against gp100 altered peptide ligands," *Cancer Immunol Immunother.*, vol. 52(4), pp. 199-206 (Apr. 2003, Epub Feb. 18, 2003).

Dionne, et al., "Her-2/neu altered peptide ligand-induced CTL responses: implications for peptieds with increased HLA affinity and T-cell-receptor interaction," *Cancer Immunol Immunother.*, vol. 53(4), pp. 307-314 (Apr. 2004, Epub Nov. 5, 2003).

Falk, et al., "Allele-specific motifs revealed by sequencing of self-peptide eluted from MHC molecules," *Nature*, vol. 351(6324), pp. 290-296 (May 23, 1991).

Fujie, et al., "A Mage-1-Encoded HLA-A24-Binding Synthetic Peptide Induces Specific Anti-Tumor Cytotoxic T Lymphocytes," *Int J Cancer*, vol. 80(2), pp. 169-172 (Jan. 18, 1999).

Gusarova, et al., "A cell-penetrating ARF peptide inhibitor of FoxM1 in mouse hepatocellular carcinoma treatment," *J Clin Invest.*, vol. 117(1), pp. 99-111 (Jan. 2007, Epub Dec. 14, 2006).

Harris, Structure and Function of the p53 Tumor Suppressor Gene: Clues for Rational Cancer Therapeutic Strategies, *J Natl Cancer Inst.*, vol. 88(20), pp. 1442-1455 (Oct. 16, 1996).

Hoffman, et al., "The Ability of Variant Peptides to Reverse the Nonresponsiveness of T Lymphocytes to the Wild-Type Sequence p53 $_{264-272}$ Epitope," *J Immunol.*, vol. 168(3), pp. 1338-1347 (Feb. 1, 2002).

Kalinichenko, et al., "Foxm1b transcription factor is essential for development of hepatocellular carcinomas and is negatively regulated by the p19ARF tumor suppressor," *Genes Dev.*, vol. 18(7), pp. 830-850 (Apr. 1, 2004).

Kikuchi, et al., "Identification of a Sart-1-Derived Peptide Capable of Inducing HLA-A24-Restricted and Tumor-Specific Cytotoxic T Lymphocytes," *Int J Cancer*, vol. 81(3), pp. 459-466 (May 5, 1999).

Kim, et al., "The Forkhead Box m1 Transcription Factor Stimulates the Proliferation of Tumor Cells during Development of Lung Cancer," *Cancer Res.*, vol. 66(4), pp. 2153-2161 (Feb. 15, 2006).

Kondo, et al., "Prominent Roles of Secondary Anchor Residues in Peptide Binding to HLAa-A24 Human Class I Molecules," *J Immunol.*, vol. 155(9), pp. 4307-4312 (Nov. 1, 1995).

Kubo, et al., "Definition of Specific Peptides Motifs for Four Major HLA-A Alleles " *J Immunol.*, vol. 152(8), pp. 3913-3924 (Apr. 15, 1994).

Laoukili, et al., "FoxM1 is required for execution of the mitotic programme and chromosome stability," *Nat Cell Biol.*, vol. 7(2), pp. 126-136 (Feb. 2005, Epub Jan. 16, 2005).

Obama, et al., "Genome-Wide Analysis of Gene Expression in Human Intrahepatic Cholangiocarcinoma," *Hepatology*, vol. 41(6), pp. 1339-1348 (Jun. 2005).

Oiso, et al., "A Newly Identified Mage-3-Derived Epitope Recognized by HLA-A24-Restricted Cytotoxic T Lymphocytes," *Int J Cancer*, vol. 81(3), pp. 387-394 (May 5, 1999).

Radhakrishnan, et al., "Identification of a Chemical Inhibitor of the Oncogenic Transcription Factor Forkhead Box M1," *Cancer Res.*, vol. 66(19), pp. 9731-9735 (Oct. 1, 2006).

Rammensee, et al., "MHC ligands and peptide motifs: first listing," *Immunogenetics*, vol. 41(4), pp. 178-228.

Rosenberg, et al., "Cancer immunotherapy: moving beyond current vaccines," *Nat Med.*, vol. 10(9), pp. 909-915 (Sep. 2004).

Takahashi, et al. "The Neuromedin U-Growth Hormone Secretagogue Receptor 1b/Neurotensin Receptor 1 Oncogenic Signaling Pathway as a Therapeutic Target for Lung Cancer," *Cancer Res.*, vol. 66(19), pp. 9408-9419 (Oct. 1, 2006).

Tanaka, et al., "Induction of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (Oct. 15, 1997).

Van Der Burg, et al., "Immunogenicity of Peptides Bound to MHC Class I Molecules Depends on the MHC-Peptide Complex Stability," *J Immunol.*, vol. 156(9), pp. 3308-3314 (May 1, 1996).

Vissers, et al., "The Renal Cell Carcinoma-associated Antigen G250 Encodes a Human Leukocyte Antigen (HLA)-A2.1-restricted Epitope Recognized by Cytotoxic T Lymphocytes," *Cancer Res.*, vol. 59(21), pp. 5554-5559 (Nov. 1, 1999).

Wang, et al., "The Forkhead Box m1b transcription factor is essential for hepatocyte DNA replication and mitosis during mouse liver regeneration," *Proc Natl Acad Sci USA*, vol. 99(26), pp. 16881-16886 (Dec. 24, 2002, Epub Dec. 13, 2002).

Wonsey, et al., "Loss of the Forkhead Transcription Factor FoxM1 Causes Centrosome Amplification and Mitotic Catastrophe," *Cancer Res.*, vol. 65(12), pp. 5181-5189 (Jun. 15, 2005).

Yokomine, et al., "FOXM1, a novel cancer-associated antigen useful for immunotherapy of cholangiocarcinoma and lung cancer," *Abstract of the 66th Annual Meeting of the Japanese Cancer Association*, pp. 164(#P-295) (2007).

Yokomine, et al., "The forkhead box M1 transcription factor as a candidate of target for anti-cancer immunotherapy," *Int J Cancer*, vol. 126(9), pp. 2153-2163 (May 1, 2010).

Yoshida, et al., "The Forkhead Box M1 Transcription Factor Contributes to the Development and Growth of Mouse Colorectal Cancer," *Gastroenterology*, vol. 132(4), pp. 1420-1431 (Apr. 2007, Epub Jan. 25, 2007).

Zaremba, et al., "Identification of an Enhancer Agonist Cytotoxic T Lymphocyte Peptide from Human Carcinoembryonic Antigen" *Cancer Res.*, vol. 57(20), pp. 4570-4577 (Oct. 15, 1997).

U.S. Appl. No. 13/536,327, 204 pages, filed Jun. 28, 2012.

International Search Report for PCT/JP2010/001005, 4 pages, mailed Mar. 16, 2010.

Roitt, et al., Immunology, M:Mir; pp. 159, 162-163, 195-196,196-199 (2000).

Dermer, "Another Anniversary for the War on Cancer," *Bio/Technology*, vol. 12, p. 320 (1994).

Engelhard, "Structure of peptides associated with MHC class I molecules," *Curr Opin Immunol.*, vol. 6(1), pp. 13-23 (Feb. 1994).

Ezzell, "Cancer "Vaccines": An Idea Whose Time has Come?," *J Nih Res.*, vol. 7, p. 46 (1995).

Freshney, Culture of Animal Cells, A Manual of Basic Technique, Alan R. Liss, Inc. (1983).

Guo, et al., "Different length peptides bind to HLA-Aw68 similarly at their ends but bulge out in the middle," *Nature*, vol. 360(6402), pp. 364-366 (Nov. 26, 1992).

Gura, "Systems for Identifying New Drugs Are Often Faulty," *Science*, vol. 278(5340), pp. 1041-1042.(Nov. 7, 1997).

Jain, "Barriers to Drug Delivery in Solid Tumors," *Sci Am.*, vol. 271(1), pp. 58-65 (Jul. 1994).

Johnson, et al., "The clinical impact of screening and other experimental tumor studies," *Cancer Treat Rev.*, vol. 2(1), pp. 1-31 (Mar. 1975).

Rammensee, et al., "MHC ligands and peptide motifs: first listing," *Immunogenetics*, vol. 41(4), pp. 178-228 (1995).

Shastri, et al., "Presentation of Endogenous Peptide/MHC Class I Complexes Is Profoundly Influenced by Specific C-Terminal Flanking Residues," *J Immunol.*, vol. 155(9), pp. 4339-4446 (Nov. 1, 1995).

Spitler, "Cancer Vaccines: The interferon Analogy," *Cancer Biother.*, vol. 10(1), pp. 1-3 (1995).

Lee, et al., "Increased Vaccine-Specific T Cell Frequency After Peptide-Based Vaccination Correlates with Increased Susceptibility to in Vitro Stimulation But Does Not Lead to Tumor Regression," *J Immunol.*, vol. 163(11), pp. 6292-6300 (Dec. 1, 1999).

Roitt, et al., Immunology, translation from English, M: Mir: pp. 160-163 (2000).

Adams, et al., "Prediction of binding to MHC class I molecules," *J Immunol Methods*, vol. 185(2), pp. 181-190 (Sep. 25, 1995).

Ishizaki, et al., "Inhibition of Tumor Growth with Antiangiogenic Cancer Vaccine Using Epitope Peptides Derived from Human Vascular Endothelial Growth Factor Receptor," *Clin Cancer Res.*, vol. 12(19), pp. 5841-5849 (Oct. 1, 2006).

(56) References Cited

OTHER PUBLICATIONS

Parker, et al., "Scheme for Ranking Potential HLA-A2 Binding Peptides Based on Independent Binding of Individual Peptide Side-Chains," *J Immunol.*, vol. 152(1), pp. 163-175 (Jan. 1, 1994).
Schueler-Furman, et al., "Structure-based prediction of binding peptides to MHC class I molecules: Application to a broad range of MHC alleles," *Protein Sci.*, vol. 9(9), pp. 1838-1846 (Sep. 2000).
NCI Cancer Bulletin, National Cancer Institute, vol. 5, No. 10, May 2008, 11 pages.
"Guidance for Industry, Clinical Considerations for Therapeutic Cancer Vaccines," U.S. Department of health and human Services, Food and Drug Administration, Center for Biologics Evaluation and Research, Oct. 2011, 16 pages.
Schwartzenruber D.J., et al., "gp100 Peptide Vaccine and Interleukin-2 in Patients with Advanced Melanoma," *The New England journal of Medicine*, 364:22, Jun. 2, 2011, 2119-2127.
Abelev, G.I., "Immunology of Human Tumors," Nature, No. 2, 2000, 16 pages.
Andre, F., et al., "Exosomes as Potent Cell-Free Peptide-Based Vaccine I Dendritic Cell-Dervied Exosomes Transfer Functional MHC Class I/Peptide Complexes to Dendritic Cells," *The Journal of Immunology*, 2004, 172:2126-2136.
Komori, H., et al, :Identification of HLA-A2- or HLA-A24-Restricted CTL Epitopes Possibly Useful for Glypican-3-Specific Immunotherapy of Hepatocellular Carcinoma, *Clinical Cancer Research*, 2006; 12(9) May 1, 2006, 2689-2697.
Laoukili, J. et al., "FoxM1: At the Crossroads of Ageing and Cancer," Biochim Biophys Acta., 2007 Jan:1775(1): 92-102 Epub Aug. 30, 2006.
Israeli Application No. 214130, cited in an Office Action issued for the corresponding Israeli Application on Aug. 18, 2013.

\* cited by examiner

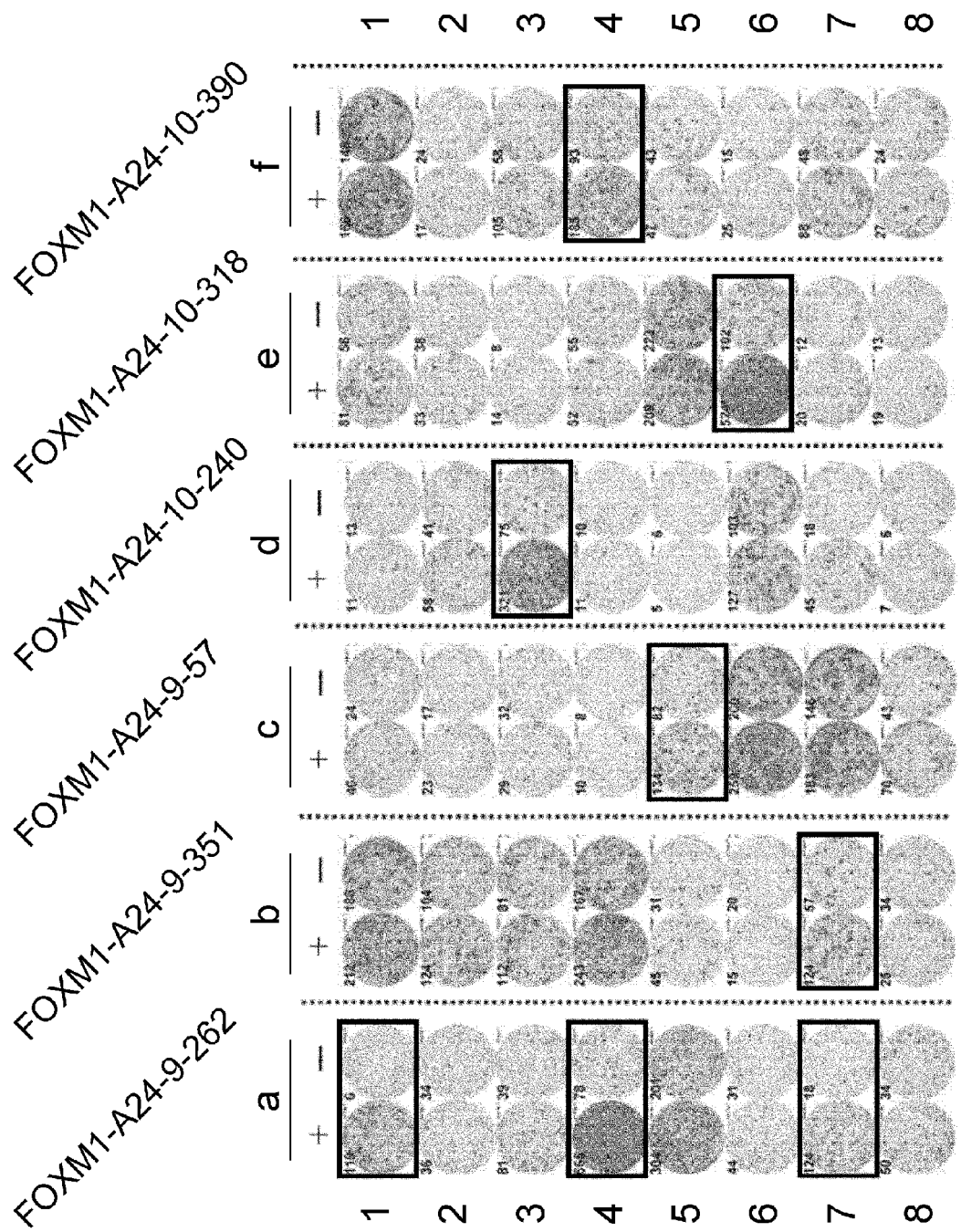
Fig. 1a-f

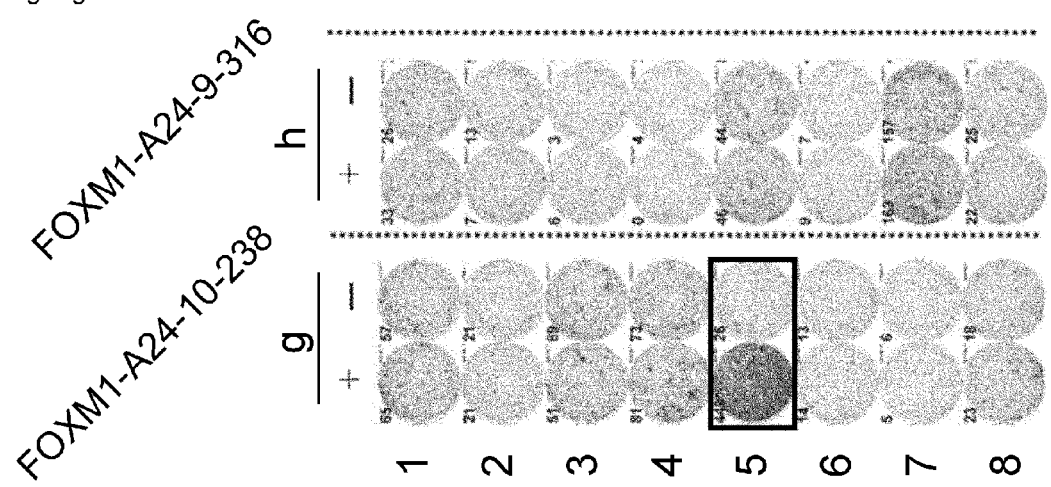
Fig. 1g-h

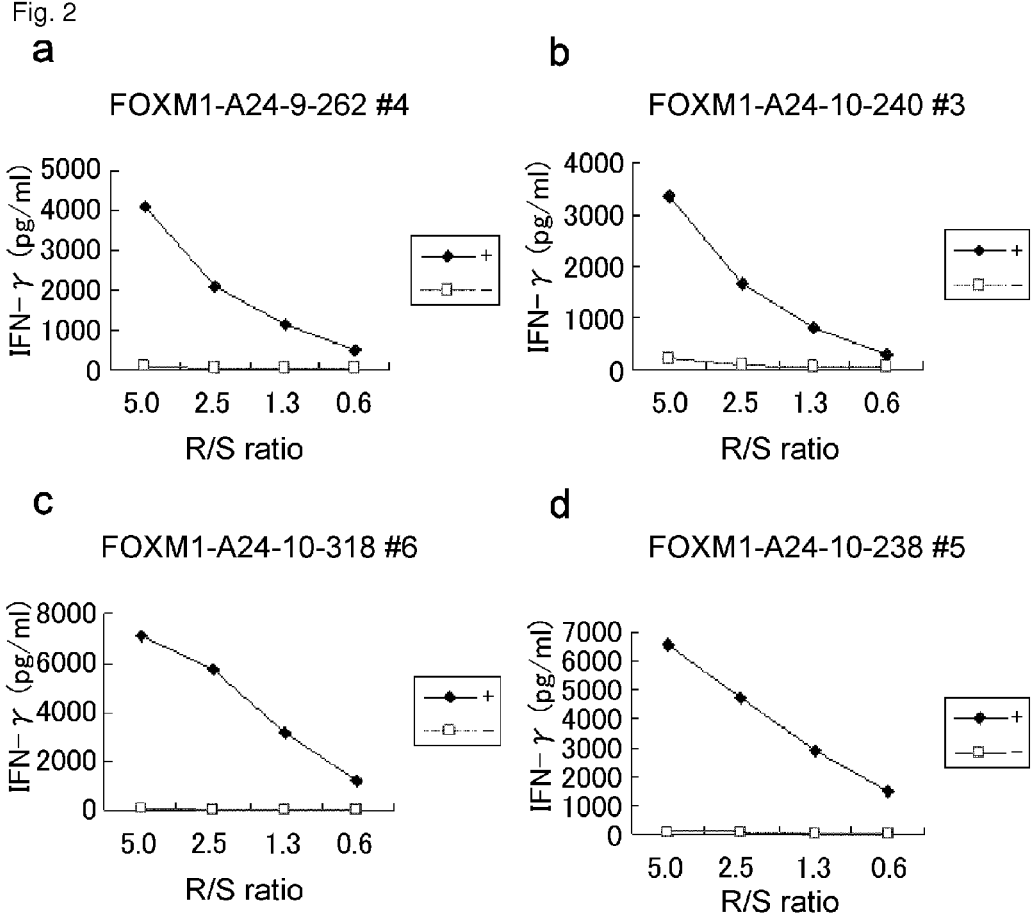

SEQUENCE LISTING

```
<160> NUMBER OF SEQ ID NOS: 38

<210> SEQ ID NO 1
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 1

Arg Tyr Leu Thr Leu Asp Gln Val Phe
1               5
```

```
<210> SEQ ID NO 2
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 2

Ile Tyr Thr Trp Ile Glu Asp His Phe
1               5

<210> SEQ ID NO 3
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 3

Leu Phe Asn Phe Ile Phe Leu Cys Leu
1               5

<210> SEQ ID NO 4
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 4

Ile Phe Leu Cys Leu Ser Val Leu Leu
1               5

<210> SEQ ID NO 5
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 5

Leu Phe Gly Glu Gly Phe Ser Pro Leu
1               5

<210> SEQ ID NO 6
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 6

Asp Phe Gly Thr Pro Ile Thr Ser Leu
1               5

<210> SEQ ID NO 7
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 7

Arg Asn Met Thr Ile Lys Thr Glu Leu
1               5

<210> SEQ ID NO 8
```

```
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 8

Lys Phe Pro Ala Gly Ile Lys Ile Ile
1               5

<210> SEQ ID NO 9
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 9

Arg Thr Glu Val Thr Leu Glu Thr Leu
1               5

<210> SEQ ID NO 10
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 10

Arg Ser Leu Thr Glu Gly Leu Val Leu
1               5

<210> SEQ ID NO 11
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 11

Val Phe Gly Tyr Met Ser Lys Phe Phe
1               5

<210> SEQ ID NO 12
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 12

Phe Phe Ser Gly Asp Leu Arg Asp Phe
1               5

<210> SEQ ID NO 13
<211> LENGTH: 9
<212> TYPE: PRT
<213> ORGANISM: Artificial
<220> FEATURE:
<223> OTHER INFORMATION: an artificially synthesized peptide sequence

<400> SEQUENCE: 13

Glu Trp Pro Ser Pro Ala Pro Ser Phe
1               5

<210> SEQ ID NO 14
<211> LENGTH: 9
<212> TYPE: PRT
```

```
<213> ORGANISM: Artificial
<220> FEATURE:
<223> OTHER INFORMATION: an artificially synthesized peptide sequence

<400> SEQUENCE: 14

Tyr Met Ala Met Ile Gln Phe Ala Ile
1               5

<210> SEQ ID NO 15
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 15

Ser Tyr Ser Gln Glu Val Gly Gly Pro Phe
1               5                   10

<210> SEQ ID NO 16
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 16

Ser Tyr Met Ala Met Ile Gln Phe Ala Ile
1               5                   10

<210> SEQ ID NO 17
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 17

Ser Phe Pro Gly Leu Asp Glu Asp Pro Leu
1               5                   10

<210> SEQ ID NO 18
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 18

Asn Phe Ile Phe Leu Cys Leu Ser Val Leu
1               5                   10

<210> SEQ ID NO 19
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 19

Gln Phe Pro Val Asn Gln Ser Leu Val Leu
1               5                   10

<210> SEQ ID NO 20
<211> LENGTH: 10
<212> TYPE: PRT
<213> ORGANISM: Artificial
<220> FEATURE:
```

-continued

<223> OTHER INFORMATION: an artificially synthesized peptide sequence

<400> SEQUENCE: 20

Leu Phe Gly Glu Gly Phe Ser Pro Leu Leu
1               5                   10

<210> SEQ ID NO 21
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 21

Lys Phe Phe Ser Gly Asp Leu Arg Asp Phe
1               5                   10

<210> SEQ ID NO 22
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 22

Lys Val Pro Leu Pro Leu Ala Ala Ser Leu
1               5                   10

<210> SEQ ID NO 23
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 23

Lys Pro Leu Asp Pro Gly Ser Pro Gln Leu
1               5                   10

<210> SEQ ID NO 24
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 24

Asp Phe Gly Thr Pro Ile Thr Ser Leu Phe
1               5                   10

<210> SEQ ID NO 25
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 25

Leu Thr Leu Asp Gln Val Phe Lys Pro Leu
1               5                   10

<210> SEQ ID NO 26
<211> LENGTH: 10
<212> TYPE: PRT
<213> ORGANISM: Artificial
<220> FEATURE:
<223> OTHER INFORMATION: an artificially synthesized peptide sequence

```
<400> SEQUENCE: 26

Arg Leu Leu Ser Ser Glu Pro Leu Asp Leu
1               5                   10

<210> SEQ ID NO 27
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 27

Arg Pro Ile Lys Val Glu Ser Pro Pro Leu
1               5                   10

<210> SEQ ID NO 28
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 28

Arg Pro Leu Ile Leu Lys Arg Arg Arg Leu
1               5                   10

<210> SEQ ID NO 29
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 29

Ser Tyr Leu Val Pro Ile Gln Phe Pro Val
1               5                   10

<210> SEQ ID NO 30
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 30

Val Leu Gln Pro Ser Val Lys Val Pro Leu
1               5                   10

<210> SEQ ID NO 31
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 31

Pro Tyr Ser Tyr Met Ala Met Ile Gln Phe
1               5                   10

<210> SEQ ID NO 32
<211> LENGTH: 10
<212> TYPE: PRT
<213> ORGANISM: Artificial
<220> FEATURE:
<223> OTHER INFORMATION: an artificially synthesized peptide sequence

<400> SEQUENCE: 32
```

Thr Trp Ile Glu Asp His Phe Pro Tyr Phe
1               5                   10

<210> SEQ ID NO 33
<211> LENGTH: 3641
<212> TYPE: DNA
<213> ORGANISM: Homo sapiens

<400> SEQUENCE: 33

| | | | | | |
|---|---|---|---|---|---|
| actgaaagct | ccggtgccag | accccacccc | cggccccggc | ccgggacccc | ctcccctccc | 60 |
| gggatccccc | ggggttccca | ccccgccccgc | accgccgggg | accggccggg | tccggcgcga | 120 |
| gcccccgtcc | ggggccctgg | ctcggccccc | aggttggagg | agcccggagc | ccgccttcgg | 180 |
| agctacggcc | taacggcggc | ggcgactgca | gtctggaggg | tccacacttg | tgattctcaa | 240 |
| tggagagtga | aaacgcagat | tcataatgaa | actagccccc | cgtcggccac | tgattctcaa | 300 |
| aagacggagg | ctgccccttc | ctgttcaaaa | tgccccaagt | gaaacatcag | aggaggaacc | 360 |
| taagagatcc | cctgcccaac | aggagtctaa | tcaagcagag | gcctccaagg | aagtggcaga | 420 |
| gtccaactct | tgcaagtttc | cagctgggat | caagattatt | aaccaccccca | ccatgcccaa | 480 |
| cacgcaagta | gtggccatcc | ccaacaatgc | taatattcac | agcatcatca | cagcactgac | 540 |
| tgccaaggga | aaagagagtg | gcagtagtgg | gcccaacaaa | ttcatcctca | tcagctgtgg | 600 |
| gggagcccca | actcagcctc | caggactccg | gcctcaaacc | caaaccagct | atgatgccaa | 660 |
| aaggacagaa | gtgaccctgg | agaccttggg | accaaaacct | gcagctaggg | atgtgaatct | 720 |
| tcctagacca | cctggagccc | tttgcgagca | gaaacgggag | acctgtgcag | atggtgaggc | 780 |
| agcaggctgc | actatcaaca | atagcctatc | caacatccag | tggcttcgaa | agatgagttc | 840 |
| tgatggactg | ggctcccgca | gcatcaagca | agagatggag | gaaaaggaga | attgtcacct | 900 |
| ggagcagcga | caggttaagg | ttgaggagcc | ttcgagacca | tcagcgtcct | ggcagaactc | 960 |
| tgtgtctgag | cggccaccct | actcttacat | ggccatgata | caattcgcca | tcaacagcac | 1020 |
| tgagaggaag | cgcatgactt | tgaaagacat | ctatacgtgg | attgaggacc | actttcccta | 1080 |
| ctttaagcac | attgccaagc | caggctggaa | gaactccatc | cgccacaacc | tttccctgca | 1140 |
| cgacatgttt | gtccgggaga | cgtctgccaa | tggcaaggtc | tccttctgga | ccattcaccc | 1200 |
| cagtgccaac | cgctacttga | cattggacca | ggtgtttaag | ccactggacc | cagggtctcc | 1260 |
| acaattgccc | gagcacttgg | aatcacagca | gaaacgaccg | aatccagagc | tccgccggaa | 1320 |
| catgaccatc | aaaaccgaac | tcccctggg | cgcacggcgg | aagatgaagc | cactgctacc | 1380 |
| acgggtcagc | tcatacctgg | tacctatcca | gttcccggtg | aaccagtcac | tggtgttgca | 1440 |
| gccctcggtg | aaggtgccat | tgcccctggc | ggcttccctc | atgagctcag | agcttgcccg | 1500 |
| ccatagcaag | cgagtccgca | ttgcccccaa | ggttttggg | gaacaggtgg | tgtttggtta | 1560 |
| catgagtaag | ttcttttagtg | gcgatctgcg | agattttggt | acacccatca | ccagcttgtt | 1620 |
| taattttatc | tttctttgtt | tatcagtgct | gctagctgag | gagggatag | ctcctctttc | 1680 |
| ttctgcagga | ccagggaaag | aggagaaact | cctgtttgga | gaagggtttt | ctccttttgct | 1740 |
| tccagttcag | actatcaagg | aggaagaaat | ccagcctggg | gaggaaatgc | cacacttagc | 1800 |
| gagacccatc | aaagtggaga | gccctccctt | ggaagagtgg | ccctcccgg | ccccatcttt | 1860 |
| caaagaggaa | tcatctcact | cctggaggga | ttcgtcccaa | tctcccaccc | caagacccaa | 1920 |
| gaagtcctac | agtgggctta | ggtccccaac | ccggtgtgtc | tcggaaatgc | ttgtgattca | 1980 |
| acacagggag | aggagggaga | ggagccggtc | tcggaggaaa | cagcatctac | tgcctccctg | 2040 |
| tgtggatgag | ccggagctgc | tcttctcaga | ggggcccagt | acttcccgct | gggccgcaga | 2100 |

```
gctcccgttc ccagcagact cctctgaccc tgcctcccag ctcagctact cccaggaagt    2160
gggaggacct tttaagacac ccattaagga aacgctgccc atctcctcca ccccgagcaa    2220
atctgtcctc cccagaaccc ctgaatcctg gaggctcacg ccccagcca aagtaggggg     2280
actggatttc agcccagtac aaacctccca gggtgcctct gaccccttgc ctgaccccct    2340
ggggctgatg gatctcagca ccactccctt gcaaagtgct ccccccttg aatcaccgca     2400
aaggctcctc agttcagaac ccttagacct catctccgtc cccctttggca actcttctcc   2460
ctcagatata gacgtcccca gccaggctc cccggagcca caggtttctg gccttgcagc     2520
caatcgttct ctgacagaag gcctggtcct ggacacaatg aatgacagcc tcagcaagat    2580
cctgctggac atcagctttc ctggcctgga cgaggaccca ctgggccctg acaacatcaa    2640
ctggtcccag tttattcctg agctacagta gagccctgcc cttgcccctg tgctcaagct    2700
gtccaccatc ccgggcactc caaggctcag tgcaccccaa gcctctgagt gaggacagca    2760
ggcagggact gttctgctcc tcatagctcc ctgctgcctg attatgcaaa agtagcagtc    2820
acaccctagc cactgctggg accttgtgtt ccccaagagt atctgattcc tctgctgtcc    2880
ctgccaggag ctgaagggtg ggaacaacaa aggcaatggt gaaagagat taggaacccc     2940
ccagcctgtt tccattctct gcccagcagt ctcttacctt ccctgatctt tgcagggtgg    3000
tccgtgtaaa tagtataaat tctccaaatt atcctctaat tataaatgta agcttatttc    3060
cttagatcat tatccagaga ctgccagaag gtgggtagga tgacctgggg tttcaattga    3120
cttctgttcc ttgcttttag ttttgataga agggaagacc tgcagtgcac ggtttcttcc    3180
aggctgaggt acctggatct tgggttcttc actgcaggga cccagacaag tggatctgct    3240
tgccagagtc cttttttgccc ctccctgcca cctcccccgtg tttccaagtc agctttcctg  3300
caagaagaaa tcctggttaa aaaagtcttt tgtattgggt caggagttga atttggggtg    3360
ggaggatgga tgcaactgaa gcagagtgtg ggtgcccaga tgtgcgctat tagatgtttc    3420
tctgataatg tccccaatca taccagggag actggcattg acgagaactc aggtggaggc    3480
ttgagaaggc cgaaagggcc cctgacctgc ctggcttcct tagcttgccc ctcagctttg    3540
caaagagcca ccctaggccc cagctgaccg catgggtgtg agccagcttg agaacactaa    3600
ctactcaata aaagcgaagg tggacaaaaa aaaaaaaaa a                        3641
```

<210> SEQ ID NO 34
<211> LENGTH: 801
<212> TYPE: PRT
<213> ORGANISM: Homo sapiens

<400> SEQUENCE: 34

```
Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Pro
            20                  25                  30

Lys Arg Ser Pro Ala Gln Gln Glu Ser Asn Gln Ala Glu Ala Ser Lys
        35                  40                  45

Glu Val Ala Glu Ser Asn Ser Cys Lys Phe Pro Ala Gly Ile Lys Ile
    50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
```

```
                100             105             110
Gly Ala Pro Thr Gln Pro Pro Gly Leu Arg Pro Gln Thr Gln Thr Ser
            115                 120             125

Tyr Asp Ala Lys Arg Thr Glu Val Thr Leu Glu Thr Leu Gly Pro Lys
130                 135                 140

Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
            180                 185                 190

Asp Gly Leu Gly Ser Arg Ser Ile Lys Gln Glu Met Glu Glu Lys Glu
            195                 200                 205

Asn Cys His Leu Glu Gln Arg Gln Val Lys Val Glu Glu Pro Ser Arg
        210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
            260                 265                 270

Phe Lys His Ile Ala Lys Pro Gly Trp Lys Asn Ser Ile Arg His Asn
            275                 280                 285

Leu Ser Leu His Asp Met Phe Val Arg Glu Thr Ser Ala Asn Gly Lys
        290                 295                 300

Val Ser Phe Trp Thr Ile His Pro Ser Ala Asn Arg Tyr Leu Thr Leu
305                 310                 315                 320

Asp Gln Val Phe Lys Pro Leu Asp Pro Gly Ser Pro Gln Leu Pro Glu
                325                 330                 335

His Leu Glu Ser Gln Gln Lys Arg Pro Asn Pro Glu Leu Arg Arg Asn
            340                 345                 350

Met Thr Ile Lys Thr Glu Leu Pro Leu Gly Ala Arg Arg Lys Met Lys
            355                 360                 365

Pro Leu Leu Pro Arg Val Ser Ser Tyr Leu Val Pro Ile Gln Phe Pro
        370                 375                 380

Val Asn Gln Ser Leu Val Leu Gln Pro Ser Val Lys Val Pro Leu Pro
385                 390                 395                 400

Leu Ala Ala Ser Leu Met Ser Ser Glu Leu Ala Arg His Ser Lys Arg
                405                 410                 415

Val Arg Ile Ala Pro Lys Val Phe Gly Glu Gln Val Val Phe Gly Tyr
            420                 425                 430

Met Ser Lys Phe Phe Ser Gly Asp Leu Arg Asp Phe Gly Thr Pro Ile
            435                 440                 445

Thr Ser Leu Phe Asn Phe Ile Phe Leu Cys Leu Ser Val Leu Leu Ala
        450                 455                 460

Glu Glu Gly Ile Ala Pro Leu Ser Ser Ala Gly Pro Gly Lys Glu Glu
465                 470                 475                 480

Lys Leu Leu Phe Gly Glu Gly Phe Ser Pro Leu Leu Pro Val Gln Thr
                485                 490                 495

Ile Lys Glu Glu Glu Ile Gln Pro Gly Glu Met Pro His Leu Ala
            500                 505                 510

Arg Pro Ile Lys Val Glu Ser Pro Pro Leu Glu Glu Trp Pro Ser Pro
        515                 520                 525
```

-continued

```
Ala Pro Ser Phe Lys Glu Glu Ser Ser His Ser Trp Glu Asp Ser Ser
    530                 535                 540
Gln Ser Pro Thr Pro Arg Pro Lys Lys Ser Tyr Ser Gly Leu Arg Ser
545                 550                 555                 560
Pro Thr Arg Cys Val Ser Glu Met Leu Val Ile Gln His Arg Glu Arg
                565                 570                 575
Arg Glu Arg Ser Arg Ser Arg Arg Lys Gln His Leu Leu Pro Pro Cys
            580                 585                 590
Val Asp Glu Pro Glu Leu Leu Phe Ser Glu Gly Pro Ser Thr Ser Arg
        595                 600                 605
Trp Ala Ala Glu Leu Pro Phe Pro Ala Asp Ser Ser Asp Pro Ala Ser
    610                 615                 620
Gln Leu Ser Tyr Ser Gln Glu Val Gly Gly Pro Phe Lys Thr Pro Ile
625                 630                 635                 640
Lys Glu Thr Leu Pro Ile Ser Ser Thr Pro Ser Lys Ser Val Leu Pro
                645                 650                 655
Arg Thr Pro Glu Ser Trp Arg Leu Thr Pro Pro Ala Lys Val Gly Gly
            660                 665                 670
Leu Asp Phe Ser Pro Val Gln Thr Ser Gln Gly Ala Ser Asp Pro Leu
        675                 680                 685
Pro Asp Pro Leu Gly Leu Met Asp Leu Ser Thr Thr Pro Leu Gln Ser
    690                 695                 700
Ala Pro Pro Leu Glu Ser Pro Gln Arg Leu Leu Ser Ser Glu Pro Leu
705                 710                 715                 720
Asp Leu Ile Ser Val Pro Phe Gly Asn Ser Ser Pro Ser Asp Ile Asp
                725                 730                 735
Val Pro Lys Pro Gly Ser Pro Glu Pro Gln Val Ser Gly Leu Ala Ala
            740                 745                 750
Asn Arg Ser Leu Thr Glu Gly Leu Val Leu Asp Thr Met Asn Asp Ser
        755                 760                 765
Leu Ser Lys Ile Leu Leu Asp Ile Ser Phe Pro Gly Leu Asp Glu Asp
    770                 775                 780
Pro Leu Gly Pro Asp Asn Ile Asn Trp Ser Gln Phe Ile Pro Glu Leu
785                 790                 795                 800
Gln
```

```
<210> SEQ ID NO 35
<211> LENGTH: 22
<212> TYPE: DNA
<213> ORGANISM: Artificial
<220> FEATURE:
<223> OTHER INFORMATION: Artificial sequence

<400> SEQUENCE: 35
gtctaccagg cattcgcttc at                                             22

<210> SEQ ID NO 36
<211> LENGTH: 24
<212> TYPE: DNA
<213> ORGANISM: Artificial
<220> FEATURE:
<223> OTHER INFORMATION: Artificial sequence

<400> SEQUENCE: 36
tcagctggac cacagccgca gcgt                                           24

<210> SEQ ID NO 37
<211> LENGTH: 21
```

```
<212> TYPE: DNA
<213> ORGANISM: Artificial
<220> FEATURE:
<223> OTHER INFORMATION: Artificial sequence

<400> SEQUENCE: 37
tcagaaatcc tttctcttga c                                      21

<210> SEQ ID NO 38
<211> LENGTH: 24
<212> TYPE: DNA
<213> ORGANISM: Artificial
<220> FEATURE:
<223> OTHER INFORMATION: Artificial sequence

<400> SEQUENCE: 38
ctagcctctg gaatcctttc tctt                                   24
```

FOXM1 PEPTIDES AND IMMUNOGENIC COMPOSITIONS CONTAINING THEM

PRIORITY

The present application is a U.S. National Stage Application of PCT/JP2010/001005, filed Feb. 17, 2010, which claims the benefit of U.S. Provisional Application No. 61/153,408, filed on Feb. 18, 2009, the entire contents of which are incorporated by reference herein in their entirety.

TECHNICAL FIELD

The present invention relates to the field of biological science, more specifically to the field of cancer therapy. In particular, the present invention relates to novel peptides that are extremely effective as cancer vaccines, and drugs for treating and preventing tumors.

BACKGROUND ART

It has been demonstrated that CD8 positive CTLs recognize epitope peptides derived from tumor-associated antigens (TAAs) on major histocompatibility complex (MHC) class I molecule, and then kill the tumor cells. Since the discovery of melanoma antigen (MAGE) family as the first example of TAAs, many other TAAs have been discovered through immunological approaches (NPL 1: Boon T, Int J Cancer 1993 May 8, 54(2): 177-80; NPL 2: Boon T & van der Bruggen P, J Exp Med 1996 Mar. 1, 183(3): 725-9), and some of the TAAs are now in the process of clinical development as immunotherapeutic targets.

Identification of new TAAs, which induce potent and specific anti-tumor immune responses, warrants further development of clinical application of peptide vaccination strategy in various types of cancer (NPL 3: Harris C C, J Natl Cancer Inst 1996 Oct. 16, 88(20): 1442-55; NPL 4: Butterfield L H et al., Cancer Res 1999 Jul. 1, 59(13): 3134-42; NPL 5: Vissers J L et al., Cancer Res 1999 Nov. 1, 59(21): 5554-9; NPL 6: van der Burg S H et al., J Immunol 1996 May 1, 156(9): 3308-14; NPL 7: Tanaka F et al., Cancer Res 1997 Oct. 15, 57(20): 4465-8; NPL 8: Fujie T et al., Int J Cancer 1999 Jan. 18, 80(2): 169-72; NPL 9: Kikuchi M et al., Int J Cancer 1999 May 5, 81(3): 459-66; NPL 10: Oiso M et al., Int J Cancer 1999 May 5, 81(3): 387-94). Until now, several clinical trials using these tumor-associated antigen derived peptides have been reported. Unfortunately, only a low objective response rate could be observed in these cancer vaccine trials so far (NPL 11: Belli F et al., J Clin Oncol 2002 Oct. 15, 20(20): 4169-80; NPL 12: Coulie P G et al., Immunol Rev 2002 October, 188: 33-42; NPL 13: Rosenberg S A et al., Nat Med 2004 September, 10(9): 909-15).

Favorable TAA is indispensable for proliferation and survival of cancer cells, as a target for immunotherapy, because the use of such TAAs may minimize the well-described risk of immune escape of cancer cells attributable to deletion, mutation, or down-regulation of TAAs as a consequence of therapeutically driven immune selection.

CITATION LIST

Non Patent Literature

[NPL 1] Boon T, Int J Cancer 1993 May 8, 54(2): 177-80
[NPL 2] Boon T & van der Bruggen P, J Exp Med 1996 Mar. 1, 183(3): 725-9
[NPL 3] Harris C C, J Natl Cancer Inst 1996 Oct. 16, 88(20): 1442-55
[NPL 4] Butterfield L H et al., Cancer Res 1999 Jul. 1, 59(13): 3134-42
[NPL 5] Vissers J L et al., Cancer Res 1999 Nov. 1, 59(21): 5554-9
[NPL 6] van der Burg S H et al., J Immunol 1996 May 1, 156(9): 3308-14
[NPL 7] Tanaka F et al., Cancer Res 1997 Oct. 15, 57(20): 4465-8
[NPL 8] Fujie T et al., Int J Cancer 1999 Jan. 18, 80(2): 169-72
[NPL 9] Kikuchi M et al., Int J Cancer 1999 May 5, 81(3): 459-66
[NPL 10] Oiso M et al., Int J Cancer 1999 May 5, 81(3): 387-94)
[NPL 11] Belli F et al., J Clin Oncol 2002 Oct. 15, 20(20): 4169-80
[NPL 12] Coulie P G et al., Immunol Rev 2002 October, 188: 33-42
[NPL 13] Rosenberg S A et al., Nat Med 2004 September, 10(9): 909-15).

SUMMARY OF INVENTION

The present invention is based, in part, on the discovery of suitable targets of immunotherapy. Because TAAs are generally perceived for the immune system as "self" and therefore often have no immunogenicity, the discovery of appropriate targets is of extreme importance. As noted above, FOXM1 (SEQ ID NO: 34 encoded by the gene of GenBank Accession No. NM_202002.1 (SEQ ID NO: 33)) has been identified as up-regulated in tissues of cancers, such as acute myeloid leukemia (AML), bladder cancer, breast cancer, cervical cancer, cholangiocellular carcinoma, chronic myeloid leukemia (CML), colorectal cancer, esophageal cancer, gastric cancer, gastric cancer diffuse-type, liver cancer, non-small cell lung cancer (NSCLC), lymphoma, osteosarcoma, ovarian cancer, pancreatic cancer, prostate cancer, renal carcinoma, small cell lung cancer (SCLC), soft tissue tumor and testicular tumor. Thus, FOXM1 is a candidate target of immunotherapy.

The present invention is based, at least in part, on the identification of specific epitope peptides of FOXM1, which possess the ability to induce cytotoxic T lymphocytes (CTLs) specific to FOXM1. As discussed in detail below, peripheral blood mononuclear cells (PBMCs) obtained from a healthy donor were stimulated using HLA-A*2402 binding candidate peptides derived from FOXM1. CTL lines with specific cytotoxicity against HLA-A24 positive target cells pulsed with each of candidate peptides were then established. These results demonstrate that these peptides are HLA-A24 restricted epitope peptides that can induce potent and specific immune responses against cells expressing FOXM1. These results demonstrate that FOXM1 is strongly immunogenic and the epitopes thereof are effective targets for tumor immunotherapy.

Accordingly, it is an object of the present invention to provide isolated peptides binding to HLA antigen, which is FOXM1 (SEQ ID NO: 34) or fragments thereof. The present peptides are expected to have CTL inducibility. They can be used to induce CTL ex vivo or can be administered to a subject for inducing immune responses against cancers such as AML, bladder cancer, breast cancer, cervical cancer, cholangiocellular carcinoma, CML, colorectal cancer, esophageal cancer, gastric cancer, gastric cancer diffuse-type, liver cancer, NSCLC, lymphoma, osteosarcoma, ovarian cancer, pancreatic cancer, prostate cancer, renal carcinoma, SCLC, soft tissue tumor and testicular tumor. Preferably, the peptides are nonapeptides or decapeptides, and more preferably, consist of the amino acid sequence selected from the group of SEQ ID NOs: 2, 7, 8, 16, 25, 30 and 31, show strong CTL inducibility.

The present invention contemplates modified peptides, having an amino acid sequence of SEQ ID NOs: 2, 7, 8, 16, 25, 30 and 31, wherein one, two or more amino acid(s) is/are substituted or added, so long as the modified peptides retain the original CTL inducibility.

Further, the present invention provides isolated polynucleotides encoding any of the peptides of the present invention. These polynucleotides can be used for inducing, or preparing antigen-expressing cells (APCs) with CTL inducibility or can be administered to a subject for inducing immune responses against cancers as well as the present peptides.

When administered to a subject, the present peptides are presented on the surface of APCs and then induce CTLs targeting the respective peptides. Therefore, it is an aspect of the present invention to provide compositions or substances including any peptides or polynucleotides of the present invention for inducing CTL. Furthermore, compositions or substances including any of the peptides or polynucleotides can be used for treating and/or for the prophylaxis of cancers, such as AML, bladder cancer, breast cancer, cervical cancer, cholangiocellular carcinoma, CML, colorectal cancer, esophageal cancer, gastric cancer, gastric cancer diffuse-type, liver cancer, NSCLC, lymphoma, osteosarcoma, ovarian cancer, pancreatic cancer, prostate cancer, renal carcinoma, SCLC, soft tissue tumor and testicular tumor, and/or for preventing post-operative recurrence thereof. Thus, it is yet another object of the present invention to provide pharmaceutical compositions or substances for treating and/or for the prophylaxis of cancers, and/or for preventing postoperative recurrence thereof, which include any of the peptides or polynucleotides of the present invention. Instead of or in addition to the present peptides or polynucleotides, the present pharmaceutical compositions or substances may include, as the active ingredients, APCs or exosomes which present any of the present peptides.

The peptides or polynucleotides of the present invention may be used to induce APCs which present on its surface a complex of an HLA antigen and the present peptide, for example, by contacting APCs derived from a subject with the present peptide or introducing a polynucleotide encoding the present peptide into APCs. Such APCs have high CTL inducibility against the target peptides and are useful for cancer immunotherapy. Therefore, it is another object of the present invention to provide methods for inducing APCs with CTL inducibility as well as APCs obtained by the methods.

It is a further object of the present invention to provide a method for inducing CTL, which includes the step of co-culturing CD8-positive cells with APCs or exosomes presenting a peptide of the present invention on its surface or the step of introducing a gene that includes a polynucleotide encoding a T cell receptor (TCR) subunit binding to the present peptide. The CTLs obtainable by the present methods also find use in treating and/or preventing cancers, such as AML, bladder cancer, breast cancer, cervical cancer, cholangiocellular carcinoma, CML, colorectal cancer, esophageal cancer, gastric cancer, gastric cancer diffuse-type, liver cancer, NSCLC, lymphoma, osteosarcoma, ovarian cancer, pancreatic cancer, prostate cancer, renal carcinoma, SCLC, soft tissue tumor and testicular tumor. Therefore, it is another object of the present invention to provide CTLs obtainable by the present methods.

Moreover, a further object of the present invention is to provide methods for inducing immune response against cancers, which methods include the step of administering substances or compositions containing FOXM1 or fragments thereof, polynucleotides encoding FOXM1 or the fragments thereof, or exosomes or APCs presenting FOXM1 or the fragments thereof.

The present invention may be applied to any diseases related to FOXM1 overexpression including cancer, such as AML, bladder cancer, breast cancer, cervical cancer, cholangiocellular carcinoma, CML, colorectal cancer, esophageal cancer, gastric cancer, gastric cancer diffuse-type, liver cancer, NSCLC, lymphoma, osteosarcoma, ovarian cancer, pancreatic cancer, prostate cancer, renal carcinoma, SCLC, soft tissue tumor and testicular tumor.

It is to be understood that both the foregoing summary of the present invention and the following detailed description are of exemplified embodiments, and not restrictive of the present invention or other alternate embodiments of the present invention.

BRIEF DESCRIPTION OF DRAWINGS

Various aspects and applications of the present invention will become apparent to the skilled artisan upon consideration of the brief description of the figures. and the detailed description of the present invention and its preferred embodiments which follows.

FIG. 1*a-f* depicts the photographs showing the results of IFN-gamma ELISPOT assay on CTLs that were induced with peptides derived from FOXM1. The CTLs in the well numbers #1, 4 and #7 stimulated with the peptides of FOXM1-A24-9-262 (SEQ ID NO: 2) (a), #7 with FOXM1-A24-9-351 (SEQ ID NO: 7) (b), #5 with FOXM1-A24-9-57 (SEQ ID NO: 8) (c), #3 with FOXM1-A24-10-240 (SEQ ID NO: 16) (d), #6 with FOXM1-A24-10-318 (SEQ ID NO: 25) (e), and #4 with FOXM1-A24-10-390 (SEQ ID NO:30) (f) showed potent IFN-gamma production compared with the control, respectively.

FIG. 1*g-h* The CTLs in the well numbers #4 with FOXM1-A24-10-238 (SEQ ID NO:31) (g) showed potent IFN-gamma production compared with the control, respectively. In contrast, as a typical case of negative data, it was not shown specific IFN-gamma production from the CTLs stimulated with the peptide of FOXM1-A24-9-316 (SEQ ID NO: 1) against peptide-pulsed target cells (h). In the figures, "+" indicates the IFN-gamma production against target cells pulsed with the appropriate peptide, and "-" indicates the IFN-gamma production against target cells not pulsed with any peptides. The square on the well of these pictures indicates that the cells from the corresponding well were expanded to establish CTL lines.

FIG. 2 depicts the line graphs showing the IFN-gamma production of the CTL lines stimulated with the peptides of FOXM1-A24-9-262 (SEQ ID NO: 2) (a), FOXM1-A24-10-240 (SEQ ID NO: 16) (b), FOXM1-A24-10-318 (SEQ ID NO: 25) (c) and FOXM1-A24-10-238 (SEQ ID NO:31) (d) detected by IFN-gamma ELISA assay. It demonstrated that CTL lines established by stimulation with each peptide showed potent IFN-gamma production compared with the control. In the figures, "+" indicates the IFN-gamma production against target cells pulsed with the appropriate peptide and "-" indicates the IFN-gamma production against target cells not pulsed with any peptides.

DESCRIPTION OF EMBODIMENTS

Figure 3:
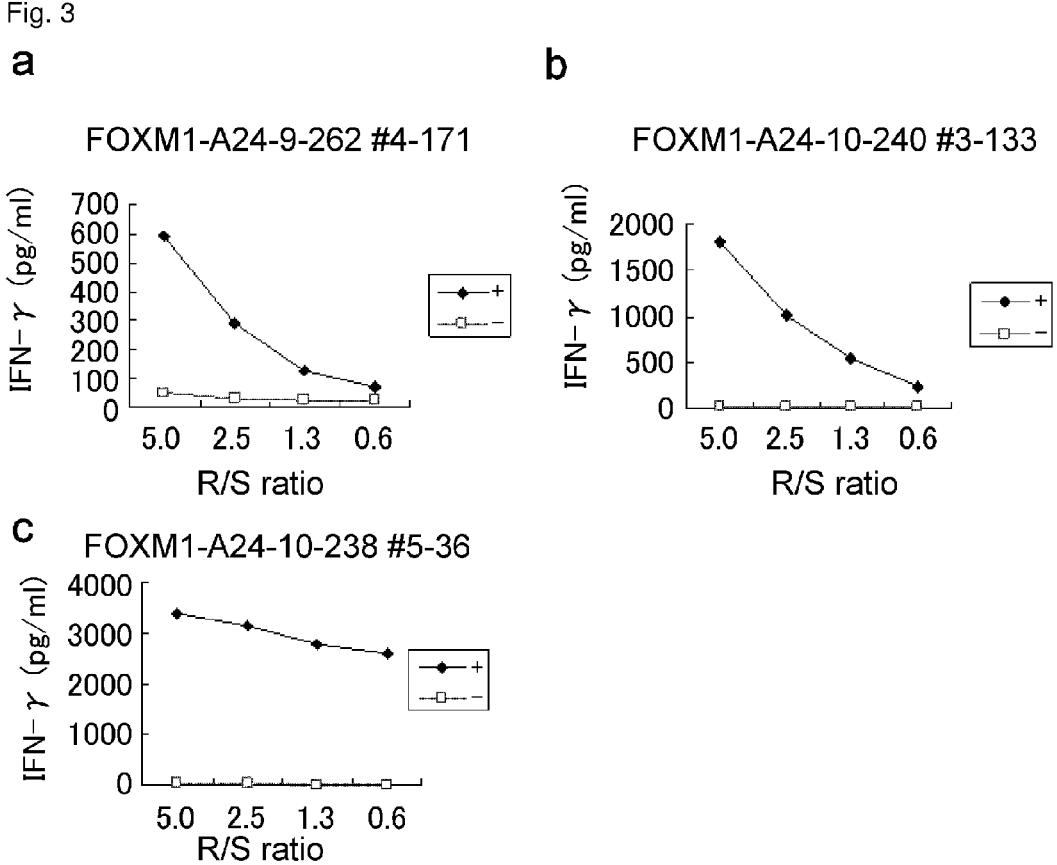
FIG. 3 shows the IFN-gamma production of the CTL clones established by limiting dilution from the CTL lines stimulated with the peptides of FOXM1-A24-9-262 (SEQ ID NO: 2) (a), FOXM1-A24-10-240 (SEQ ID NO: 16) (b) and FOXM1-A24-10-238 (SEQ ID NO: 31) (c). It demonstrated that the CTL clones established by stimulation with each peptide showed potent IFN-gamma production compared with the control. In the figures, "+" indicates the IFN-gamma production against target cells pulsed with the each peptide and "-" indicates the IFN-gamma production against target cells not pulsed with any peptides.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the present invention is not entitled to antedate such disclosure by virtue or prior invention.

In case of conflict, the present specification, including definitions, will control. In addition, the materials, methods, and examples are illustrative only and not intended to be limiting.

I. DEFINITIONS

The words "a", "an", and "the" as used herein mean "at least one" unless otherwise specifically indicated.

The terms "polypeptide", "peptide" and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "amino acid" as used herein refers to naturally occurring and synthetic amino acids, as well as amino acid analogs and amino acid mimetics that similarly function to the naturally occurring amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotides", "nucleotides" and "nucleic acids" are used interchangeably herein and, unless otherwise specifically indicated are similarly to the amino acids referred to by their commonly accepted single-letter codes.

Unless otherwise defined, the term "cancer" refers to the cancers overexpressing FOXM1 gene, examples of which include, but are not limited to, AML, bladder cancer, breast cancer, cervical cancer, cholangiocellular carcinoma, CML, colorectal cancer, esophageal cancer, gastric cancer, gastric cancer diffuse-type, liver cancer, NSCLC, lymphoma, osteosarcoma, ovarian cancer, pancreatic cancer, prostate cancer, renal carcinoma, SCLC, soft tissue tumor and testicular tumor.

Unless otherwise defined, the terms "cytotoxic T lymphocyte", "cytotoxic T cell" and "CTL" are used interchangeably herein and unless otherwise specifically indicated, refer to a sub-group of T lymphocytes that are capable of recognizing non-self cells (e.g., tumor cells, virus-infected cells) and inducing the death of such cells.

Unless otherwise defined, all technical and scientific terms used herein have the same meaning as commonly understood by one of ordinary skill in the art to which the present invention belongs.

II. PEPTIDES

To demonstrate that peptides derived from FOXM1 function as antigens recognized by CTLs, peptides derived from FOXM1 (SEQ ID NO: 34) were analyzed to determine whether they were antigen epitopes restricted by HLA-A24 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994).

Candidates of HLA-A24 binding peptides derived from FOXM1 were identified based on their binding affinities to HLA-A24. The following peptides are the candidate peptides:

FOXM1-A24-9-316 (SEQ ID NO: 1),
FOXM1-A24-9-262 (SEQ ID NO: 2),
FOXM1-A24-9-451 (SEQ ID NO: 3),
FOXM1-A24-9-455 (SEQ ID NO: 4),
FOXM1-A24-9-483 (SEQ ID NO: 5),
FOXM1-A24-9-443 (SEQ ID NO: 6),
FOXM1-A24-9-351 (SEQ ID NO: 7),
FOXM1-A24-9-57 (SEQ ID NO: 8),
FOXM1-A24-9-133 (SEQ ID NO: 9),
FOXM1-A24-9-754 (SEQ ID NO: 10),
FOXM1-A24-9-429 (SEQ ID NO: 11),
FOXM1-A24-9-436 (SEQ ID NO: 12),
FOXM1-A24-9-524 (SEQ ID NO: 13),
FOXM1-A24-9-241 (SEQ ID NO: 14),
FOXM1-A24-10-627 (SEQ ID NO: 15),
FOXM1-A24-10-240 (SEQ ID NO: 16),
FOXM1-A24-10-777 (SEQ ID NO: 17),
FOXM1-A24-10-453 (SEQ ID NO: 18),
FOXM1-A24-10-382 (SEQ ID NO: 19),
FOXM1-A24-10-483 (SEQ ID NO: 20),

FOXM1-A24-10-435 (SEQ ID NO: 21),
FOXM1-A24-10-396 (SEQ ID NO: 22),
FOXM1-A24-10-325 (SEQ ID NO: 23),
FOXM1-A24-10-443 (SEQ ID NO: 24),
FOXM1-A24-10-318 (SEQ ID NO: 25),
FOXM1-A24-10-713 (SEQ ID NO: 26),
FOXM1-A24-10-513 (SEQ ID NO: 27),
FOXM1-A24-10-7 (SEQ ID NO: 28),
FOXM1-A24-10-376 (SEQ ID NO: 29),
FOXM1-A24-10-390 (SEQ ID NO: 30),
FOXM1-A24-10-238 (SEQ ID NO: 31), and
FOXM1-A24-10-264 (SEQ ID NO: 32).

After in vitro stimulation of T-cells by dendritic cells (DCs) loaded with these peptides, CTLs were successfully established using each of the following peptides:
FOXM1-A24-9-262 (SEQ ID NO: 2),
FOXM1-A24-9-351 (SEQ ID NO: 7),
FOXM1-A24-9-57 (SEQ ID NO: 8),
FOXM1-A24-10-240 (SEQ ID NO: 16),
FOXM1-A24-10-318 (SEQ ID NO: 25),
FOXM1-A24-10-390 (SEQ ID NO: 30), and
FOXM1-A24-10-238 (SEQ ID NO: 31).
These established CTLs show potent specific CTL activity against target cells pulsed with respective peptides. These results demonstrate that FOXM1 is an antigen recognized by CTL and that the peptides tested are epitope peptides of FOXM1 restricted by HLA-A24.

Since the FOXM1 gene is over expressed in cancer cells of such as AML, bladder cancer, breast cancer, cervical cancer, cholangiocellular carcinoma, CML, colorectal cancer, esophageal cancer, gastric cancer, gastric cancer diffuse-type, liver cancer, NSCLC, lymphoma, osteosarcoma, ovarian cancer, pancreatic cancer, prostate cancer, renal carcinoma, SCLC, soft tissue tumor and testicular tumor and not expressed in most normal organs, it is a good target for immunotherapy. Thus, the present invention provides nonapeptides (peptides consisting of nine amino acid residues) and decapeptides (peptides consisting of ten amino acid residues) corresponding to CTL-recognized epitopes of FOXM1. Alternatively, the present invention provides an isolated peptide which binds to an HLA antigen and induces cytotoxic T lymphocytes (CTL), wherein the peptide consists of the amino acid sequence of SEQ ID NO: 34 or is an immunologically active fragment thereof. Preferred examples of nonapeptides and decapeptides of the present invention include those peptides consisting of the amino acid sequence selected among SEQ ID NOs: 2, 7, 8, 16, 25, 30 and 31.

Generally, software programs presently available, for example, on the Internet, such as those described in Parker K C et al., J Immunol 1994 Jan. 1, 152(1): 163-75, Buus et al. (Tissue Antigens., 62:378-84, 2003) and Nielsen et al. (Protein Sci., 12:1007-17, 2003, Bioinformatics, 20(9):1388-97, 2004), can be used to calculate the binding affinities between various peptides and HLA antigens in silico. Binding affinity with HLA antigens can be measured as described, for example, in the references to Parker K C et al., J Immunol 1994 Jan. 1, 152(1): 163-75; and Kuzushima K et al., Blood 2001, 98(6): 1872-81. The methods for determining binding affinity is described, for example, in; Journal of Immunological Methods, 1995, 185: 181-190; Protein Science, 2000, 9: 1838-1846. Therefore, one can select fragments derived from FOXM1, which have high binding affinity with HLA antigens using such software programs. Thus, the present invention encompasses peptides consisting of any fragments derived from FOXM1 which bind with HLA antigens identified using such known programs. The peptide of the present invention may be the peptide consisting of the full length of FOXM1.

The peptides of the present invention can be flanked with additional amino acid residues so long as the resulting peptide retains its CTL inducibility. The amino acid residues to be flanked to the present peptides may be composed of any kind of amino acids so long as they do not impair the CTL inducibility of the original peptide. Thus, the present invention encompasses peptides which include the peptides derived from FOXM1 and have binding affinity to HLA antigens. Such peptides are typically less than about 40 amino acids, often less than about 20 amino acids, usually less than about 15 amino acids.

In general, the modification of one, two or more amino acids in a peptide will not influence the function of the peptide, and in some cases will even enhance the desired function of the original protein. In fact, modified peptides (i.e., peptides composed of an amino acid sequence in which one, two or several amino acid residues have been modified (i.e., substituted, deleted, added or inserted as compared to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention may have both CTL inducibility and an amino acid sequence selected from among SEQ ID NOs: 2, 7, 8, 16, 25, 30 and 31, wherein one, two or even more amino acids are added, inserted and/or substituted.

Those skilled in the art recognize that individual additions or substitutions to an amino acid sequence which alters a single amino acid or a small percentage of amino acids tend to result in the conservation of the properties of the original amino acid side-chain. As such, they are often referred to as "conservative substitutions" or "conservative modifications", wherein the alteration of a protein results in a modified protein having a function analogous to the original protein. Conservative substitution tables providing functionally similar amino acids are well known in the art. Examples of amino acid side chain characteristics that are desirable to conserve include, for example, hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are accepted in the art as conservative substitutions for one another:

1) Alanine (A), Glycine (G);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V);
  6) Phenylalanine (F), Tyrosine (Y), Tryptophan (W);
  7) Serine (S), Threonine (T); and
  8) Cysteine (C), Methionine (M) (see, e.g., Creighton, Proteins 1984).

Such conservatively modified peptides are also considered to be peptides of the present invention. However, peptides of the present invention are not restricted thereto and can include non-conservative modifications, so long as the modified peptide retains the CTL inducibility of the original peptide. Furthermore, modified peptides should not exclude CTL inducible peptides of polymorphic variants, interspecies homologues, and alleles of FOXM1.

To retain the requisite CTL inducibility one can modify (insert, delete, add and/or substitute) a small number (for example, 1, 2 or several) or a small percentage of amino acids. Herein, the term "several" means 5 or fewer amino acids, for example, 4, 3 or fewer. The percentage of amino acids to be modified is preferably 20% or less, more preferably 15% of less, even more preferably 10% or less or 1 to 5%.

Moreover, peptides of the present invention can be inserted, substituted or added with amino acid residues or amino acid residues may be deleted to achieve a higher binding affinity. When used in the context of immunotherapy, the present peptides should be presented on the surface of a cell or exosome, preferably as a complex with an HLA antigen. In addition to peptides that are naturally displayed, since the regularity of the sequences of peptides displayed by binding to HLA antigens is already known (J Immunol 1994, 152: 3913; Immunogenetics 1995, 41: 178; J Immunol 1994, 155: 4307), modifications based on such regularity can be introduced into the immunogenic peptides of the present invention. For example, it may be desirable to substitute the second amino acid from the N-terminus substituted with phenylalanine, tyrosine, methionine, or tryptophan, and/or the amino acid at the C-terminus with phenylalanine, leucine, isoleucine, tryptophan, or methionine in order to increase the HLA-A24 binding. Thus, peptides having the amino acid sequences selected from the group consisting of SEQ ID NOs: 2, 7, 8, 16, 25, 30 and 31, wherein the second amino acid from the N-terminus of the amino acid sequence of the SEQ ID NOs is substituted with phenylalanine, tyrosine, methionine, or tryptophan, and peptides, and/or wherein the C-terminus of the amino acid sequence of the SEQ ID NOs is substituted with phenylalanine, leucine, isoleucine, tryptophan, or methionine are encompassed by the present invention.

The present invention also contemplates the addition of one, two or several amino acids to the N and/or C-terminus of the described peptides. Such modified peptides having high HLA antigen binding affinity and retained CTL inducibility are also included in the present invention.

However, when the peptide sequence is identical to a portion of the amino acid sequence of an endogenous or exogenous protein having a different function, side effects such as autoimmune disorders and/or allergic symptoms against specific substances may be induced. Therefore, it is preferable to first perform homology searches using available databases to avoid situations in which the sequence of the peptide matches the amino acid sequence of another protein. When it becomes clear from the homology searches that there exists not even a peptide with 1 or 2 amino acid differences as compared to the objective peptide, the objective peptide can be modified in order to increase its binding affinity with HLA antigens, and/or increase its CTL inducibility without any danger of such side effects.

Although peptides having high binding affinity to the HLA antigens as described above are expected to be highly effective, the candidate peptides, which are selected according to the presence of high binding affinity as an indicator, are further examined for the presence of CTL inducibility. Herein, the phrase "CTL inducibility" indicates the ability of the peptide to induce CTLs when presented on antigen-presenting cells (APCs). Further, "CTL inducibility" includes the ability of the peptide to induce CTL activation, CTL proliferation, promote CTL lysis of target cells, and to increase CTL IFN-gamma production.

Confirmation of CTL inducibility is accomplished by inducing APCs carrying human MHC antigens (for example, B-lymphocytes, macrophages, and dendritic cells (DCs)), or more specifically DCs derived from human peripheral blood mononuclear leukocytes, and after stimulation with the peptides, mixing with CD8-positive cells, and then measuring the IFN-gamma produced and released by CTL against the target cells. As the reaction system, transgenic animals that have been produced to express a human HLA antigen (for example, those described in BenMohamed L, Krishnan R, Longmate J, Auge C, Low L, Primus J, Diamond D J, Hum Immunol 2000 August, 61(8): 764-79, Related Articles, Books, Linkout Induction of CTL response by a minimal epitope vaccine in HLA A*0201/DR1 transgenic mice: dependence on HLA class II restricted T(H) response) can be used. For example, the target cells can be radio-labeled with $^{51}Cr$ and such, and cytotoxic activity can be calculated from radioactivity released from the target cells. Alternatively, CTL inducibility can be assessed by measuring IFN-gamma produced and released by CTL in the presence of APCs that carry immobilized peptides, and visualizing the inhibition zone on the media using anti-IFN-gamma monoclonal antibodies.

As a result of examining the CTL inducibility of the peptides as described above, it was discovered that nonapeptides or decapeptides selected from peptides consisting of the amino acid sequences indicated by SEQ ID NOs: 2, 7, 8, 16, 25, 30 and 31 showed particularly high CTL inducibility as well as high binding affinity to an HLA antigen. Thus, these peptides are exemplified as preferred embodiments of the present invention.

Furthermore, the result of homology analysis showed that those peptides do not have significant homology with peptides derived from any other known human gene products. This lowers the possibility of unknown or undesired immune responses when used for immunotherapy. Therefore, also from this aspect, these peptides find use for eliciting immunity in cancer patients against FOXM1. Thus, the peptides of the present invention, preferably, peptides consisting of the amino acid sequence selected from the group consisting of SEQ ID NOs: 2, 7, 8, 16, 25, 30 and 31.

In addition to the modification of the present peptides discussed above, the described peptides can be further linked to other substances, so long as they retain the CTL inducibility of the original peptide. Exemplary substances include: peptides, lipids, sugar and sugar chains, acetyl groups, natural and synthetic polymers, etc. The present peptides can contain modifications such as glycosylation, side chain oxidation, and/or phosphorylation; so long as the modifications do not destroy the biological activity of the original peptide. These kinds of modifications may confer additional functions (e.g., targeting function, and delivery function) and/or stabilize the peptides.

For example, to increase the in vivo stability of a polypeptide, it is known in the art to introduce D-amino acids, amino acid mimetics or unnatural amino acids; this concept can also be adopted to the present polypeptides. The stability of a polypeptide can be assayed in a number of ways. For instance, peptidases and various biological media, such as human plasma and serum, can be used to test stability (see, e.g., Verhoef et al., Eur J Drug Metab Pharmacokin 1986, 11: 291-302).

Moreover, as noted above, among the modified peptides that are substituted, deleted or added by one, two or several amino acid residues, those having same or higher activity as compared to original peptides can be screened for or selected. The present invention, therefore, also provides the method of screening for or selecting modified peptides having same or higher activity as compared to originals. For example, the method can comprise steps of:

a: substituting, deleting or adding at least one amino acid residue of a peptide of the present invention:
b: determining the activity of said peptide:
c: selecting the peptide having same or higher activity as compared to the original.

Herein, the peptides of the present invention can also be described as "FOXM1 peptide(s)" or "FOXM1 polypeptide(s)".

III. PREPARATION OF FOXM1 PEPTIDES

The peptides of the present invention can be prepared using well known techniques. For example, the peptides can be prepared synthetically, using recombinant DNA technology or chemical synthesis. The peptides of the present invention can be synthesized individually or as longer polypeptides composed of two or more peptides. The peptides can then be isolated i.e., purified or isolated so as to be substantially free of other naturally occurring host cell proteins and fragments thereof, or any other chemical substances.

The peptides of the present invention may contain modifications, such as glycosylation, side chain oxidation, or phosphorylation; so long as the modifications do not destroy the biological activity of the peptides as described herein. Other modifications include incorporation of D-amino acids or other amino acid mimetics that can be used, for example, to increase the serum half life of the peptides.

A peptide of the present invention can be obtained through chemical synthesis based on the selected amino acid sequence. Examples of conventional peptide synthesis methods that can be adapted to the synthesis include, but are not limited to:
(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the present peptides can be obtained adapting any known genetic engineering methods for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. The host cell is then cultured to produce the peptide of interest. The peptide can also be produced in vitro adapting an in vitro translation system.

IV. POLYNUCLEOTIDES

The present invention also provides polynucleotides which encode any of the aforementioned peptides of the present invention. These include polynucleotides derived from the natural occurring FOXM1 gene (GenBank Accession No. NM_202002.1 (SEQ ID NO: 33)) as well as those having a conservatively modified nucleotide sequences thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. As is well known in the art, a DNA molecule is composed of bases such as the naturally occurring bases A, T, C, and G, and T is replaced by U in an RNA. One of skill will recognize that non-naturally occurring bases be included in polynucleotides, as well.

The polynucleotide of the present invention can encode multiple peptides of the present invention with or without intervening amino acid sequences. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J 1984, 3: 801-5.

V. EXOSOMES

The present invention further provides intracellular vesicles called exosomes, which present complexes formed between the peptides of the present invention and HLA antigens on their surface. Exosomes can be prepared, for example, by using the methods detailed in Japanese Patent Application Kohyo Publications Nos. Hei 11-510507 and WO99/03499, and can be prepared using APCs obtained from patients who are subject to treatment and/or prevention. The exosomes of the present invention can be inoculated as vaccines, in a fashion similar to the peptides of the present invention.

The type of HLA antigens contained in the complexes must match that of the subject requiring treatment and/or prevention. For example, in the Japanese population, HLA-A24 (particularly, A*2402) are prevalent and therefore would be appropriate for treatment of a Japanese patient. The use of the A24 type that is highly expressed among the Japanese and Caucasian is favorable for obtaining effective results. Typically, in the clinic, the type of HLA antigen of the patient requiring treatment is investigated in advance, which enables the appropriate selection of peptides having high levels of binding affinity to the particular antigen, or having CTL inducibility by antigen presentation. Furthermore, in order to obtain peptides having both high binding affinity and CTL inducibility, substitution, insertion and/or addition of 1, 2, or several amino acids can be performed based on the amino acid sequence of the naturally occurring FOXM1 partial peptide.

When using the A24 type HLA antigen for the exosome of the present invention, the peptides having a sequence of any one of SEQ ID NOs: 2, 7, 8, 16, 25, 30 and 31 find use.

VI. ANTIGEN-PRESENTING CELLS (APCs)

The present invention also provides isolated APCs that present complexes formed between HLA antigens and the peptides of the present invention on its surface. The APCs can be derived from patients who are subject to treatment and/or prevention, and can be administered as vaccines by themselves or in combination with other drugs including the peptides of the present invention, exosomes, or CTLs.

The APCs are not limited to a particular kind of cells and include DCs, Langerhans cells, macrophages, B cells, and activated T cells, which are known to present proteinaceous antigens on their cell surface so as to be recognized by lymphocytes. Since DC is a representative APC having the strongest CTL inducing action among APCs, DCs find use as the APCs of the present invention.

For example, the APCs of the present invention can be obtained by inducing DCs from peripheral blood monocytes and then contacting (stimulating) them with the peptides of the present invention in vitro, ex vivo or in vivo. When the peptides of the present invention are administered to the subjects, APCs that present the peptides of the present invention are induced in the body of the subject. Therefore, the APCs of the present invention can be obtained by collecting the APCs from the subject after administering the peptides of the present invention to the subject. Alternatively, the APCs of the present invention can be obtained by contacting APCs collected from a subject with the peptide of the present invention.

The APCs of the present invention can be administered alone or in combination with other drugs including the peptides, exosomes or CTLs of the present invention to a subject for inducing immune response against cancer in the subject. For example, the ex vivo administration can include steps of:
a: collecting APCs from a first subject,
b: contacting the APCs of step a, with the peptide and
c: administering the APCs of step b to a second subject.

The first subject and the second subject can be the same individual, or may be different individuals. The APCs obtained by step b can be administered as a vaccine for treating and/or preventing cancer including AML, bladder cancer, breast cancer, cervical cancer, cholangiocellular carcinoma, CML, colorectal cancer, esophageal cancer, gastric cancer, gastric cancer diffuse-type, liver cancer, NSCLC, lymphoma, osteosarcoma, ovarian cancer, pancreatic cancer, prostate cancer, renal carcinoma, SCLC, soft tissue tumor and testicular tumor.

The present invention also provides a method or process for manufacturing a pharmaceutical composition inducing APCs, wherein the method includes the step of admixing or formulating the peptide of the present invention with a pharmaceutically acceptable carrier.

According to an aspect of the present invention, the APCs have a high level of CTL inducibility. In the term of "high level of CTL inducibility", the high level is relative to the level of that by APC contacting with no peptide or peptides which cannot induce the CTL. Such APCs having a high level of CTL inducibility can be prepared by a method which includes the step of transferring a polynucleotide encoding the peptide of the present invention to APCs in vitro as well as the method mentioned above. The introduced genes can be in the form of DNAs or RNAs. Examples of methods for introduction include, without particular limitations, various methods conventionally performed in this field, such as lipofection, electroporation, and calcium phosphate method. More specifically, it can be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present peptides.

VII. CYTOTOXIC T LYMPHOCYTES (CTLs)

A CTL induced against any of the peptides of the present invention strengthens the immune response targeting cancer cells in vivo and thus can be used as vaccines in a fashion similar to the peptides per se. Thus, the present invention also provides isolated CTLs that are specifically induced or activated by any of the present peptides.

Such CTLs can be obtained by (1) administering the peptide(s) of the present invention to a subject, collecting CTLs from the subject; or (2) contacting (stimulating) subject-derived APCs, and CD8-positive cells, or peripheral blood mononuclear leukocytes in vitro with the peptide(s) of the present invention and then isolating CTLs; or (3) contacting CD8-positive cells or peripheral blood mononuclear leukocytes in vitro with APCs or exosomes presenting a complex of an HLA antigen and the present peptide on its surface and then isolating CTLs; or (4) introducing a gene including a polynucleotide encoding a T cell receptor (TCR) subunit binding to the peptide of the present invention to the CTLs. The aforementioned APCs and exosomes can be prepared by methods described above and the method of (4) is detailed bellow in section "VIII. T cell receptor (TCR)".

The CTLs of the present invention can be derived from patients who are subject to treatment and/or prevention, and can be administered by themselves or in combination with other drugs including the peptides of the present invention or exosomes for the purpose of regulating effects. The obtained CTLs act specifically against target cells presenting the peptides of the present invention, for example, the same peptides used for induction. The target cells can be cells that endogenously express FOXM1, such as cancer cells, or cells that are transfected with the FOXM1 gene; and cells that present a peptide of the present invention on the cell surface due to stimulation by the peptide can also serve as targets of activated CTL attack.

VIII. T CELL RECEPTOR (TCR)

The present invention also provides a composition containing nucleic acids encoding polypeptides that are capable of forming a subunit of a T cell receptor (TCR), and methods of using the same. The TCR subunits have the ability to form TCRs that confer specificity to T cells against tumor cells expressing FOXM1. By using the known methods in the art, the nucleic acids of alpha- and beta-chains as the TCR subunits of the CTL induced with one or more peptides of the present invention can be identified (WO2007/032255 and Morgan et al., J Immunol, 171, 3288 (2003)). For example, the PCR method is preferred to analyze the TCR. The PCR primers for the analysis can be, for example, 5'-R primers (5'-gtctaccaggcattcgcttcat-3') as 5' side primers (SEQ ID NO: 35) and 3-TRa-C primers (5'-tcagctggaccacagccgcagcgt-3') specific to TCR alpha chain C region (SEQ ID NO: 36), 3-TRb-C1 primers (5'-tcagaaatcctttctcttgac-3') specific to TCR beta chain C1 region (SEQ ID NO: 37) or 3-TRbeta-C2 primers (5'-ctagcctctggaatcctttctctt-3') specific to TCR beta chain C2 region (SEQ ID NO: 38) as 3' side primers, but not limited. The derivative TCRs can bind target cells displaying the FOXM1 peptide with high avidity, and optionally mediate efficient killing of target cells presenting the FOXM1 peptide in vivo and in vitro.

The nucleic acids encoding the TCR subunits can be incorporated into suitable vectors, e.g., retroviral vectors. These vectors are well known in the art. The nucleic acids or the vectors containing them usefully can be transferred into a T cell, for example, a T cell from a patient. Advantageously, the present invention provides an off-the-shelf composition allowing rapid modification of a patient's own T cells (or those of another mammal) to rapidly and easily produce modified T cells having excellent cancer cell killing properties.

The specific TCR is a receptor capable of specifically recognizing a complex of a peptide of the present invention and HLA molecule, giving a T cell specific activity against the target cell when the TCR on the surface of the T cell. A specific recognition of the above complex may be confirmed by any known methods, and preferred methods include, for example, tetramer analysis using HLA molecule and peptide of the present invention, and ELISPOT assay. By performing the ELISPOT assay, it can be confirmed that a T cell expressing the TCR on the cell surface recognizes a cell by the TCR, and that the signal is transmitted intracellularly. The confirmation that the above-mentioned complex can give a T cell cytotoxic activity when the complex exists on the T cell surface may also be carried out by a known method. A preferred method includes, for example, the determination of cytotoxic activity against an HLA positive target cell, such as chromium release assay.

Also, the present invention provides CTLs which are prepared by transduction with the nucleic acids encoding the TCR subunits polypeptides that bind to the FOXM1 peptide of, e.g., SEQ ID NOs: 2, 7, 8, 16, 25, 30 and 31 in the context of HLA-A24. The transduced CTLs are capable of homing to cancer cells in vivo, and can be expanded by well known in vitro culturing methods (e.g., Kawakami et al., J Immunol., 142, 3452-3461 (1989)). The CTLs of the present invention can be used to form an immunogenic composition useful in treating or the prevention of cancer in a patient in need of therapy or protection (WO2006/031221).

IX. PHARMACEUTICAL SUBSTANCES OR COMPOSITIONS

Prevention and prophylaxis include any activity which reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis include a wide range of prophylactic therapies aimed at alleviating the severity of the particular disorder, e.g., reducing the proliferation and metastasis of tumors, reducing angiogenesis. Treating and/or for the prophylaxis of cancer or, and/or the prevention of postoperative recurrence thereof includes any of the following steps, such as surgical removal of cancer cells, inhibition of the growth of cancerous cells, involution or regression of a tumor, induction of remission and suppression of occurrence of cancer, tumor regression, and reduction or inhibition of metastasis. Effectively treating and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

Since FOXM1 expression is specifically elevated in cancers including AML, bladder cancer, breast cancer, cervical cancer, cholangiocellular carcinoma, CML, colorectal cancer, esophageal cancer, gastric cancer, gastric cancer diffuse-type, liver cancer, NSCLC, lymphoma, osteosarcoma, ovarian cancer, pancreatic cancer, prostate cancer, renal carcinoma, SCLC, soft tissue tumor and testicular tumor, as compared with normal tissue, the peptides of the present invention or polynucleotides encoding such peptides can be used for the treatment and/or for the prophylaxis of cancer or tumor, and/or prevention of postoperative recurrence thereof. Thus, the present invention provides a pharmaceutical substance or composition for treating and/or for the prophylaxis of cancer or tumor, and/or prevention of postoperative recurrence thereof, which includes one or more of the peptides of the present invention, or polynucleotides encoding the peptides as an active ingredient. Alternatively, the present peptides can be expressed on the surface of any of the foregoing exosomes or cells, such as APCs for the use as pharmaceutical substances or compositions. In addition, the aforementioned CTLs which target any of the peptides of the present invention can also be used as the active ingredient of the present pharmaceutical substances or compositions.

In another embodiment, the present invention also provides the use of an active ingredient selected from among:
 (a) a peptide of the present invention;
 (b) a nucleic acid encoding such a peptide as disclosed herein in an expressible form;
 (c) an APC or an exosome presenting a peptide of the present invention on its surface; and
 (d) a cytotoxic T cell of the present invention
in manufacturing a pharmaceutical composition or substance for treating cancer or tumor.

Alternatively, the present invention further provides an active ingredient selected from among:
 (a) a peptide of the present invention;
 (b) a nucleic acid encoding such a peptide as disclosed herein in an expressible form;
 (c) an APC or an exosome presenting a peptide of the present invention on its surface; and
 (d) a cytotoxic T cell of the present invention for use in treating cancer of tumor.

Alternatively, the present invention further provides a method or process for manufacturing a pharmaceutical composition or substance for treating cancer or tumor, wherein the method or process includes the step of formulating a pharmaceutically or physiologically acceptable carrier with an active ingredient selected from among:

(a) a peptide of the present invention;
(b) a nucleic acid encoding such a peptide as disclosed herein in an expressible form;
(c) an APC or an exosome presenting a peptide of the present invention on its surface; and
(d) a cytotoxic T cell of the present invention
as active ingredients.

In another embodiment, the present invention also provides a method or process for manufacturing a pharmaceutical composition or substance for treating cancer or tumor, wherein the method or process includes the steps of admixing an active ingredient with a pharmaceutically or physiologically acceptable carrier, wherein the active ingredient is selected from among:

(a) a peptide of the present invention;
(b) a nucleic acid encoding such a peptide as disclosed herein in an expressible form;
(c) an APC or an exosome presenting a peptide of the present invention on its surface; and
(d) a cytotoxic T cell of the present invention.

Alternatively, the pharmaceutical composition or substance or the present invention may be used for either or both the prophylaxis of cancer or tumor and prevention of postoperative recurrence thereof.

The present pharmaceutical substances or compositions find use as a vaccine. In the context of the present invention, the phrase "vaccine" (also referred to as an "immunogenic composition") refers to a substance that has the function to induce anti-tumor immunity upon inoculation into animals.

The pharmaceutical substances or compositions of the present invention can be used to treat and/or prevent cancers or tumors, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

According to the present invention, peptides having an amino acid sequence of any one of SEQ ID NOs: 2, 7, 8, 16, 25, 30 and 31 have been found to be HLA-A24 restricted epitope peptides or candidates that can induce potent and specific immune response. Therefore, the present pharmaceutical substances or compositions which include any of these peptides having the amino acid sequences of SEQ ID NOs: 2, 7, 8, 16, 25, 30 and 31 are particularly suited for the administration to subjects whose HLA antigen is HLA-A24. The same applies to pharmaceutical substances and compositions which include polynucleotides encoding any of these peptides (i.e., the polynucleotides of the present invention).

Cancers or tumors to be treated by the pharmaceutical substances or compositions of the present invention are not limited and include any cancer or tumor in which FOXM1 is involved (e.g., is overexpressed), including, for example, AML, bladder cancer, breast cancer, cervical cancer, cholangiocellular carcinoma, CML, colorectal cancer, esophageal cancer, gastric cancer, gastric cancer diffuse-type, liver cancer, NSCLC, lymphoma, osteosarcoma, ovarian cancer, pancreatic cancer, prostate cancer, renal carcinoma, SCLC, soft tissue tumor and testicular tumor.

The present pharmaceutical substances or compositions can contain in addition to the aforementioned active ingredients, other peptides which have the ability to induce CTLs against cancerous cells, other polynucleotides encoding the other peptides, other cells that present the other peptides, or such. Herein, the other peptides that have the ability to induce CTLs against cancerous cells are exemplified by cancer specific antigens (e.g., identified TAAs), but are not limited thereto.

If needed, the pharmaceutical substances or compositions of the present invention can optionally include other therapeutic substances as an active ingredient, so long as the substance does not inhibit the antitumoral effect of the active ingredient, e.g., any of the present peptides. For example, formulations can include anti-inflammatory substances, pain killers, chemotherapeutics, and the like. In addition to including other therapeutic substances in the medicament itself, the medicaments of the present invention can also be administered sequentially or concurrently with the one or more other pharmacologic substances. The amounts of medicament and pharmacologic substance depend, for example, on what type of pharmacologic substance(s) is/are used, the disease being treated, and the scheduling and routes of administration.

It should be understood that in addition to the ingredients particularly mentioned herein, the pharmaceutical substances or compositions of the present invention can include other compositions conventional in the art having regard to the type of formulation in question.

In one embodiment of the present invention, the present pharmaceutical substances or compositions can be included in articles of manufacture and kits containing materials useful for treating the pathological conditions of the disease to be treated, e.g., cancer. The article of manufacture can include a container of any of the present pharmaceutical substances or compositions with a label. Suitable containers include bottles, vials, and test tubes. The containers can be formed from a variety of materials, such as glass or plastic. The label on the container should indicate the composition is used for treating or prevention of one or more conditions of the disease. The label can also indicate directions for administration and so on.

In addition to the container described above, a kit including a pharmaceutical substance or composition of the present invention can optionally further include a second container housing a pharmaceutically-acceptable diluent. It can further include other materials desirable from a commercial and user standpoint, including other buffers, diluents, filters, needles, syringes, and package inserts with instructions for use.

The pharmaceutical substances or compositions can, if desired, be presented in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical Substances or Compositions Containing the Peptides as the Active Ingredient The peptides of the present invention can be administered directly as a pharmaceutical substance or composition, or if necessary, that has been formulated by conventional formulation methods. In the latter case, in addition to the peptides of the present invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical substances or compositions can contain as necessary, stabilizers, suspensions, preservatives, surfactants and such. The pharmaceutical substances or compositions of the present invention can be used for anticancer purposes.

The peptides of the present invention can be prepared as a combination composed of two or more of the peptides of the present invention, to induce CTLs in vivo. The peptide combination can take the form of a cocktail or can be conjugated to each other using standard techniques. For example, the peptides can be chemically linked or expressed as a single fusion polypeptide sequence. The peptides in the combination can be the same or different. By administering the peptides of the present invention, the peptides are presented at a high density by the HLA antigens on APCs, then CTLs that specifically react toward the complex formed between the displayed peptide and the HLA antigen are induced. Alternatively, APCs (e.g., DCs) are removed from subjects and then stimulated by the peptides of the present invention to obtain APCs that present any of the peptides of this invention on their cell surface. These APCs are readministered to the subjects to induce CTLs in the subjects, and as a result, aggressiveness towards the tumor-associated endothelium can be increased.

The pharmaceutical substances or compositions for the treatment and/or prevention of cancer or tumor, which include a peptide of the present invention as the active ingredient, can also include an adjuvant known to effectively induce cellular immunity. Alternatively, the pharmaceutical substances or compositions can be administered with other active ingredients or administered by formulation into granules. An adjuvant refers to a compound that enhances the immune response against the protein when administered together (or successively) with the protein having immunological activity. Adjuvants contemplated herein include those described in the literature (Clin Microbiol Rev 1994, 7: 277-89). Example of suitable adjuvants include aluminum phosphate, aluminum hydroxide, alum, cholera toxin, *salmonella* toxin, and such, but are not limited thereto.

Furthermore, liposome formulations, granular formulations in which the peptide is bound to few-micrometers diameter beads, and formulations in which a lipid is bound to the peptide may be conveniently used.

In another embodiment of the present invention, the peptides of the present invention may also be administered in the form of a pharmaceutically acceptable salt. Preferable examples of the salts include salts with an alkali metal, salts with a metal, salts with an organic base, salts with an organic acid and salts with an inorganic acid.

In some embodiments, the pharmaceutical substances or compositions of the present invention may further include a component which primes CTLs. Lipids have been identified as substances capable of priming CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, *E. coli* lipoproteins, such as tripalmitoyl-S-glycerylcysteinyl-seryl-serine (P3CSS) can be used to prime CTL when covalently attached to an appropriate peptide (see, e.g., Deres et al., Nature 1989, 342: 561-4).

The method of administration can be oral, intradermal, subcutaneous, intravenous injection, or such, and systemic administration or local administration to the vicinity of the targeted sites. The administration can be performed by single administration or boosted by multiple administrations. The dose of the peptides of the present invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once in a few days to few months. One skilled in the art can appropriately select a suitable dose.

(2) Pharmaceutical Substances or Compositions Containing Polynucleotides as the Active Ingredient The pharmaceutical substances or compositions of the present invention can also contain nucleic acids encoding the peptides disclosed herein in an expressible form. Herein, the phrase "in an expressible form" means that the polynucleotide, when introduced into a cell, will be expressed in vivo as a polypeptide that induces anti-tumor immunity. In an exemplified embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization, e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a subject can be either direct, in which case the subject is directly exposed to a polynucleotide-carrying vector, or indirect, in which case, cells are first transformed with the polynucleotide of interest in vitro, then the cells are transplanted into the subject. Theses two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology which can also be used for the present invention are described in eds. Ausubel et al., Current Protocols in Molecular Biology, John Wiley & Sons, NY, 1993; and Krieger, Gene Transfer and Expression, A Laboratory Manual, Stockton Press, NY, 1990.

The method of administration can be oral, intradermal, subcutaneous, intravenous injection, or such, and systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of the present invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once every a few days to once every few months. One skilled in the art can appropriately select the suitable dose.

X. METHODS USING THE PEPTIDES, EXOSOMES, APCs AND CTLs

The peptides and polynucleotides of the present invention can be used for inducing APCs and CTLs. The exosomes and APCs of the present invention can be also used for inducing CTLs. The peptides, polynucleotides, exosomes and APCs can be used in combination with any other compounds so long as the compounds do not inhibit their CTL inducibility. Thus, any of the aforementioned pharmaceutical substances or compositions of the present invention can be used for inducing CTLs, and in addition thereto, those including the peptides and polynucleotides can be also used for inducing APCs as discussed explained below.

(1) Method of Inducing Antigen-Presenting Cells (APCs)

The present invention provides methods of inducing or preparing APCs with high CTL inducibility using the peptides or polynucleotides of the present invention.

The methods of the present invention include the step of contacting APCs with the peptides of the present invention in vitro, ex vivo or in vivo. For example, the method contacting APCs with the peptides ex vivo can include the steps of:
a: collecting APCs from a subject: and
b: contacting the APCs of step a with the peptide.

The APCs are not limited to a particular kind of cells and include DCs, Langerhans cells, macrophages, B cells, and activated T cells, which are known to present proteinaceous antigens on their cell surface so as to be recognized by lymphocytes. DCs can be preferably used due to its strongest CTL inducibility among the APCs. Any peptides of the present invention can be used as the peptide of step b by themselves or in combination with other peptides of the present invention.

Alternatively, the peptides of the present invention may be administered to a subject to contact the peptides with APCs in vivo. Consequently, APCs with high CTL inducibility can be induced in the body of the subject. Thus, the present invention also contemplates a method of administering the peptides of the present invention to a subject to induce APCs in vivo. It is also possible to administer polynucleotides encoding the peptides of the present invention to a subject in an expressible form, so that the peptides of the present invention are expressed and contacted with APCs in vivo, to consequently induce APCs with high CTL inducibility in the body of the subject. Thus, the present invention also contemplates a method of administering the polynucleotides of the present invention to a subject to induce APCs in vivo. The phrase "expressible form" is defined above in section "IX. Pharmaceutical substances or compositions.

(2) Pharmaceutical Substances or Compositions Containing Polynucleotides as the Active Ingredient".

Furthermore, the present invention includes introducing the polynucleotide of the present invention into an APC to induce or prepare APCs with CTL inducibility. For example, the method may include the steps of:
a: collecting APCs from a subject: and
b: introducing a polynucleotide encoding a peptide of the present invention.

Step b can be performed as described above in section "VI. Antigen-presenting cells".

Alternatively, the present invention provides a method for preparing an antigen-presenting cell (APC) which specifically induces CTL activity against FOXM1, wherein the method comprises one of the following steps:
(a) contacting an APC with a peptide of the present invention in vitro, ex vivo or in vivo; and
(b) introducing a polynucleotide encoding a peptide of the present invention into an APC.

(2) Method of Inducing CTLs

Furthermore, the present invention provides methods for inducing CTLs using the peptides, polynucleotides, or exosomes or APCs of the present invention.

The present invention also provides methods for inducing CTLs using a polynucleotide encoding a polypeptide that is capable of forming a T cell receptor (TCR) subunit recognizing a complex of the peptides of the present invention and HLA antigens. Preferably, the methods for inducing CTLs include at least one step selected from the group consisting of:
a) contacting a CD8-positive T cell with an antigen-presenting cell and/or an exosome that presents on its surface a complex of an HLA antigen and a peptide of the preset invention; and
b) introducing a polynucleotide encoding a polypeptide that is capable of forming a TCR subunit recognizing a complex of a peptide of the present invention and an HLA antigen into a CD8 positive cell.

When the peptides, the polynucleotides, APCs, or exosomes of the present invention are administered to a subject, CTLs are induced in the body of the subject, and the strength of the immune response targeting the cancer cells is enhanced. Thus, the present invention also contemplates a method which includes the step of administering the peptides, the polynucleotides, the APCs or exosomes of the present invention to a subject to induce CTLs.

Alternatively, CTLs can be also induced by their ex vivo use. In such case, after the induction of CTLs, the activated CTLs would be returned to the subject. For example, a method of the present invention to induce CTLs can include steps of:
a) collecting APCs from a subject;
b) contacting the APCs of step a) with the peptide; and
c) co-culturing the APCs of step b with CD8-positive cells.

The APCs to be co-cultured with the CD8-positive cells in above step c can also be prepared by transferring a gene that includes a polynucleotide of the present invention into APCs as described above in section "VI. Antigen-presenting cells"; but are not limited thereto and any APCs which effectively presents on its surface a complex of an HLA antigen and the peptide of the present invention can be used for the instant method.

Instead of such APCs, the exosomes that presents on its surface a complex of an HLA antigen and the peptide of the present invention can be also used. Namely, the present invention also contemplates a method wherein exosomes presenting on its surface a complex of an HLA antigen and the peptide of the present invention are co-cultured with CD8-positive cells. Such exosomes may be prepared by the methods described above in section "V. Exosomes".

Furthermore, CTL can be induced by introducing a gene that includes a polynucleotide encoding the TCR subunit binding to the peptide of the present invention into CD8-positive cells. Such transduction can be performed as described above in section "VIII. T cell receptor (TCR)".

In addition, the present invention provides a method or process for manufacturing a pharmaceutical substance or composition inducing CTLs, wherein the method includes the step of admixing or formulating the peptide of the present invention with a pharmaceutically acceptable carrier.

(3) Method of Inducing Immune Response

Moreover, the present invention provides methods for inducing immune response against diseases related to FOXM1. Suitable disease include cancer, examples of which include AML, bladder cancer, breast cancer, cervical cancer, cholangiocellular carcinoma, CML, colorectal cancer, esophageal cancer, gastric cancer, gastric cancer diffuse-type, liver cancer, NSCLC, lymphoma, osteosarcoma, ovarian cancer, pancreatic cancer, prostate cancer, renal carcinoma, SCLC, soft tissue tumor and testicular tumor.

The methods include the step of administering substances or compositions containing any of the peptides of the present invention or polynucleotides encoding them. The present inventive method also contemplates the administration of exosomes or APCs presenting any of the peptides of the present invention. For details, see the item of "IX. Pharmaceutical substances or compositions", particularly the part describing the use of the pharmaceutical substances or compositions of the present invention as vaccines. In addition, the exosomes and APCs that can be employed for the present methods for inducing immune response are described in detail under the items of "V. Exosomes", "VI. Antigen-presenting cells (APCs)", and (1) and (2) of "X. Methods using the peptides, exosomes, APCs and CTLs", supra.

The present invention also provides a method or process for manufacturing a pharmaceutical substance or composition inducing immune response, wherein the method includes the step of admixing or formulating the peptide of the present invention with a pharmaceutically acceptable carrier.

Alternatively, the method of the present invention may include the step of administrating a vaccine or a pharmaceutical composition, which contains:

(a) a peptide of the present invention;
(b) a nucleic acid encoding such a peptide as disclosed herein in an expressible form;
(c) an APC or an exosome presenting a peptide of the present invention on its surface; and
(d) a cytotoxic T cell of the present invention In the present invention, cancer overexpressing FOXM1 can be treated with these active ingredients. The cancer includes, but is not limited to, AML, bladder cancer, breast cancer, cervical cancer, cholangiocellular carcinoma, CML, colorectal cancer, esophageal cancer, gastric cancer, gastric cancer diffuse-type, liver cancer, NSCLC, lymphoma, osteosarcoma, ovarian cancer, pancreatic cancer, prostate cancer, renal carcinoma, SCLC, soft tissue tumor and testicular tumor. Accordingly, prior to the administration of the vaccines or pharmaceutical compositions containing the active ingredients, it is preferable to confirm whether the expression level of FOXM1 in the cancer cells or tissues to be treated is enhanced compared with normal cells of the same organ. Thus, in one embodiment, the present invention provides a method for treating cancer (over) expressing FOXM1, which method may include the steps of:

i) determining the expression level of FOXM1 in cancer cells or tissue obtained from a subject with the cancer to be treated;
ii) comparing the expression level of FOXM1 with normal control; and
iii) administrating at least one component selected from the group consisting of (a) to (d) described above to a subject with cancer overexpressing FOXM1 compared with normal control. Alternatively, the present invention also provides a vaccine or pharmaceutical composition containing at least one component selected from the group consisting of (a) to (d) described above, for use in administrating to a subject having cancer overexpressing FOXM1. In other words, the present invention further provides a method for identifying a subject to be treated with the FOXM1 polypeptide of the present invention, which method may include the step of determining an expression level of FOXM1 in subject-derived cancer cells or tissue, wherein an increase of the level compared to a normal control level of the gene indicates that the subject has cancer which may be treated with the FOXM1 polypeptide of the present invention. The method of treating cancer of the present invention will be described in more detail below.

A subject to be treated by the present method is preferably a mammal. Exemplary mammals include, but are not limited to, e.g., human, non-human primate, mouse, rat, dog, cat, horse, and cow.

According to the present invention, the expression level of FOXM1 in the cancer cells or tissues obtained from a subject is determined. The expression level can be determined at the transcription (nucleic acid) product level, using methods known in the art. For example, the mRNA of FOXM1 may be quantified using probes by hybridization methods (e.g., Northern hybridization). The detection may be carried out on a chip or an array. The use of an array is preferable for detecting the expression level of FOXM1. Those skilled in the art can prepare such probes utilizing the sequence information of FOXM1. For example, the cDNA of FOXM1 may be used as the probes. If necessary, the probes may be labeled with a suitable label, such as dyes, fluorescent substances and isotopes, and the expression level of the gene may be detected as the intensity of the hybridized labels.

Furthermore, the transcription product of FOXM1 (e.g., SEQ ID NO: 34) may be quantified using primers by amplification-based detection methods (e.g., RT-PCR). Such primers can also be prepared based on the available sequence information of the gene.

Specifically, a probe or primer used for the present method hybridizes under stringent, moderately stringent, or low stringent conditions to the mRNA of FOXM1. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degrees C. lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degrees C. for short probes or primers (e.g., 10 to 50 nucleotides) and at least about 60 degrees C. for longer probes or primers. Stringent conditions may also be achieved with the addition of destabilizing substances, such as formamide.

Alternatively, the translation product may be detected for the diagnosis of the present invention. For example, the quantity of FOXM1 protein (SEQ ID NO: 34) may be determined. Methods for determining the quantity of the protein as the translation product include immunoassay methods that use an antibody specifically recognizing the protein. The antibody may be monoclonal or polyclonal. Furthermore, any fragment or modification (e.g., chimeric antibody, scFv, Fab, F(ab')2, Fv, etc.) of the antibody may be used for the detection, so long as the fragment or modified antibody retains the binding ability to FOXM1 protein. Methods to prepare these kinds of antibodies for the detection of proteins are well known in the art, and any method may be employed in the present invention to prepare such antibodies and equivalents thereof.

As another method to detect the expression level of FOXM1 gene based on its translation product, the intensity of staining may be observed via immunohistochemical analysis using an antibody against FOXM1 protein. Namely, in this measurement, strong staining indicates increased presence of the protein/level and, at the same time, high expression level of FOXM1 gene.

The expression level of a target gene, e.g., including FOXM1 gene, in cancer cells can be determined to be increased if the level increases from the control level (e.g., the level in normal cells) of the corresponding the target gene by, for example, 10%, 25%, or 50%; or increases to more than 1.1 fold, more than 1.5 fold, more than 2.0 fold, more than 5.0 fold, more than 10.0 fold, or more.

The control level may be determined at the same time with the cancer cells by using a sample(s) previously collected and stored from a subject/subjects whose disease state(s) (cancerous or non-cancerous) is/are known. In addition, normal cells obtained from non-cancerous regions of an organ that has the cancer to be treated may be used as normal control. Alternatively, the control level may be determined by a statistical method based on the results obtained by analyzing previously determined expression level(s) of FOXM1 gene in samples from subjects whose disease states are known. Furthermore, the control level can be derived from a database of expression patterns from previously tested cells. Moreover, according to an aspect of the present invention, the expression level of FOXM1 gene in a biological sample may be compared to multiple control levels, which are determined from multiple reference samples. It is preferred to use a control level determined from a reference sample derived from a tissue type similar to that of the subject-derived biological sample. Moreover, it is preferred, to use the standard value of the expression levels of FOXM1 gene in a population with a known disease state. The standard value may be obtained by any method known in the art. For example, a range of mean+/−2 S.D. or mean+/−3 S.D. may be used as the standard value.

In the context of the present invention, a control level determined from a biological sample that is known to be non-cancerous is referred to as a "normal control level". On the other hand, if the control level is determined from a cancerous biological sample, it is referred to as a "cancerous control level".

When the expression level of FOXM1 gene is increased as compared to the normal control level or is similar/equivalent to the cancerous control level, the subject may be diagnosed with cancer to be treated. More specifically, the present invention provides a method of (i) diagnosing whether a subject has the cancer to be treated, and/or (ii) selecting a subject for cancer treatment, which method includes the steps of:

a) determining the expression level of FOXM1 in cancer cells or tissue(s) obtained from a subject who is suspected to have the cancer to be treated;

b) comparing the expression level of FOXM1 with a normal control level;

c) diagnosing the subject as having the cancer to be treated, if the expression level of FOXM1 is increased as compared to the normal control level; and d) selecting the subject for cancer treatment, if the subject is diagnosed as having the cancer to be treated, in step c).

Alternatively, such a method includes the steps of:

a) determining the expression level of FOXM1 in cancer cells or tissue(s) obtained from a subject who is suspected to have the cancer to be treated;

b) comparing the expression level of FOXM1 with a cancerous control level;

c) diagnosing the subject as having the cancer to be treated, if the expression level of FOXM1 is similar or equivalent to the cancerous control level; and d) selecting the subject for cancer treatment, if the subject is diagnosed as having the cancer to be treated, in step c).

The present invention also provides a kit for determining a subject suffering from cancer which can be treated with the FOXM1 polypeptide of the present invention, which may also be useful in assessing and/or monitoring the efficacy of a cancer immunotherapy. Preferably, the cancer includes, but is not limited to, AML, bladder cancer, breast cancer, cervical cancer, cholangiocellular carcinoma, CML, colorectal cancer, esophageal cancer, gastric cancer, gastric cancer diffuse-type, liver cancer, NSCLC, lymphoma, osteosarcoma, ovarian cancer, pancreatic cancer, prostate cancer, renal carcinoma, SCLC, soft tissue tumor and testicular tumor. More particularly, the kit preferably includes at least one reagent for detecting the expression of the FOXM1 gene in a subject-derived cancer cell, which reagent may be selected from the group of:

(a) a reagent for detecting mRNA of the FOXM1 gene;
(b) a reagent for detecting the FOXM1 protein; and
(c) a reagent for detecting the biological activity of the FOXM1 protein.

Suitable reagents for detecting mRNA of the FOXM1 gene include nucleic acids that specifically bind to or identify the FOXM1 mRNA, such as oligonucleotides which have a complementary sequence to a portion of the FOXM1 mRNA. These kinds of oligonucleotides are exemplified by primers and probes that are specific to the FOXM1 mRNA. These kinds of oligonucleotides may be prepared based on methods well known in the art. If needed, the reagent for detecting the FOXM1 mRNA may be immobilized on a solid matrix. Moreover, more than one reagent for detecting the FOXM1 mRNA may be included in the kit.

On the other hand, suitable reagents for detecting the FOXM1 protein include antibodies to the FOXM1 protein. The antibody may be monoclonal or polyclonal. Furthermore, any fragment or modification (e.g., chimeric antibody, scFv, Fab, F(ab')2, Fv, etc.) of the antibody may be used as the reagent, so long as the fragment or modified antibody retains the binding ability to the FOXM1 protein. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of antibodies to their targets are well known in the art, and any labels and methods may be employed for the present invention. Moreover, more than one reagent for detecting the FOXM1 protein may be included in the kit.

The kit may contain more than one of the aforementioned reagents. For example, tissue samples obtained from subjects without cancer or suffering from cancer or not may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers include bottles, vials, and test tubes. The containers may be formed from a variety of materials, such as glass or plastic.

In an embodiment of the present invention, when the reagent is a probe against the FOXM1 mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of a test sample, the number of sites displaying a detectable signal provides a quantitative indication of the amount of FOXM1 mRNA present in the sample. The detection sites may be configured in any suitably detectable shape and are typically in the shape of a bar or dot spanning the width of a test strip.

The kit of the present invention may further include a positive control sample or FOXM1 standard sample. The positive control sample of the present invention may be prepared by collecting FOXM1 positive samples and then assaying their FOXM1 levels. Alternatively, a purified FOXM1 protein or polynucleotide may be added to cells that do not express FOXM1 to form the positive sample or the FOXM1 sample. In the present invention, purified FOXM1 may be a recombinant protein. The FOXM1 level of the positive control sample is, for example, more than the cut off value.

The following examples are presented to illustrate the present invention and to assist one of ordinary skill in making and using the same. The examples are not intended in any way to otherwise limit the scope of the present invention.

EXAMPLES

Materials and Methods
Cell Lines

TISI, HLA-A*2402 positive B-lymphoblastoid cell line, was purchased from the IHWG Cell and Gene Bank (Seattle, Wash.). COS7, African green monkey kidney cell line, was purchased from ATCC.

Candidate Selection of Peptides Derived from FOXM1

9mer and 10mer peptides derived from FOXM1 that bind to HLA-A*2402 molecule were predicted using binding prediction software "BIMAS" (www-bimas.cit.nih.gov/molbio/hla_bind) (Parker et al. (J Immunol 1994, 152(1): 163-75), Kuzushima et al. (Blood 2001, 98(6): 1872-81)) and "NetMHC 3.0" (www.cbs.dtu.dk/services/NetMHC/) (Buus et al. (Tissue Antigens., 62:378-84, 2003), Nielsen et al. (Protein Sci., 12:1007-17, 2003, Bioinformatics, 20(9):1388-97, 2004)). These peptides were synthesized by Biosynthesis (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide at 20 mg/ml and stored at −80 degrees C.

In Vitro CTL Induction

Monocyte-derived dendritic cells (DCs) were used as antigen-presenting cells to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells (PBMCs) isolated from a normal volunteer (HLA-A*2402 positive) by Ficoll-Plaque (Pharmacia) solution were separated by adherence to a plastic tissue culture dish (Becton Dickinson) so as to enrich them as the monocyte fraction. The monocyte-enriched population was cultured in the presence of 1000 U/ml of granulocyte-macrophage colony-stimulating factor (R&D System) and 1000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 micro-g/ml of each of the synthesized peptides in the presence of 3 micro-g/ml of beta2-microglobulin for 3 hrs at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by X-irradiation (20 Gy) and mixed at a 1:20 ratio with autologous CD8+ T cells, obtained by positive selection with CD8 Positive Isolation Kit (Dynal). These cultures were set up in 48-well plates (Corning); each well contained $1.5 \times 10^4$ peptide-pulsed DCs, $3 \times 10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On days 7 and 14, the T cells were further stimulated with the autologous peptide-pulsed DCs. The DCs were prepared each time by the same way described above. CTLs were tested against peptide-pulsed TISI cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Watanabe T et al., Cancer Sci 2005 August, 96(8): 498-506; Suda T et al., Cancer Sci 2006 May, 97(5): 411-9).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 February, 2(2): 216-23). A total of $5 \times 10^4$ CTLs were suspended in 25 ml of AIM-V/5% AS medium with 2 kinds of human B-lymphoblastoid cell lines, inactivated by Mitomycin C, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Watanabe T et al., Cancer Sci 2005 August, 96(8): 498-506; Suda T et al., Cancer Sci 2006 May, 97(5): 411-9).

Establishment of CTL Clones

The dilutions were made to have 0.3, 1, and 3 CTLs/well in 96 round-bottomed micro titer plate (Nalge Nunc International). CTLs were cultured with $1 \times 10^4$ cells/well of 2 kinds of human B-lymphoblastoid cell lines, 30 ng/ml of anti-CD3 antibody, and 125 IU/ml of IL-2 in a total of 150 micro-l/well of AIM-V Medium containing 5% AS. 50 micro-l/well of IL-2 were added to the medium 10 days later so to reach a final concentration of 125 U/ml IL-2. CTL activity was tested on the 14th day, and CTL clones were expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, interferon (IFN)-gamma enzyme-linked immunospot (ELISPOT) assay and IFN-gamma enzyme-linked immunosorbent assay (ELISA) were performed. Specifically, peptide-pulsed TISI ($1\times10^4$ cells/well) was prepared as stimulator cells. Cultured cells in 48 wells were used as responder cells. IFN-gamma ELISPOT assay and IFN-gamma ELISA assay were performed under manufacture procedure.

Plasmid Transfection

The cDNA encoding an open reading frame of target genes or HLA-A*2402 was amplified by PCR. The PCR-amplified products were cloned into pCAGGS vector. The plasmids were transfected into COST, which is the target genes and HLA-A24 negative cell line, using lipofectamine 2000 (Invitrogen) according to the manufacturer's recommended procedures. After 2 days from transfection, the transfected cells were harvested with versene (Invitrogen) and used as the target cells ($5\times10^4$ cells/well) for CTL activity assay.

Results

Prediction of HLA-A24 Binding Peptides Derived from FOXM1

Tables 1a and 1b show the HLA-A24 binding 9mer and 10mer peptides of FOXM1 in the order of high binding affinity. 29 peptides (SEQ ID NOs: 1-12 and SEQ ID NOs: 15-31) were predicted by BIMAS and 3 peptides (SEQ ID NOs: 13-14 and SEQ ID NO: 32) were predicted by NetMHC 3.0. A total of 32 peptides with potential HLA-A24 binding ability were selected and examined to determine the epitope peptides.

TABLE 1a

HLA-A24 binding 9mer peptides derived from FOXM1

| Start Position | amino acid sequence | score | SEQ ID NO |
|---|---|---|---|
| 316 | RYLTLDQVF | 432 | 1 |
| 262 | IYTWIEDHF | 140 | 2 |
| 451 | LFNFIFLCL | 50.4 | 3 |
| 455 | IFLCLSVLL | 36 | 4 |
| 483 | LFGEGFSPL | 28.8 | 5 |
| 443 | DFGTPITSL | 20 | 6 |
| 351 | RNMTIKTEL | 18.48 | 7 |
| 57 | KFPAGIKII | 15 | 8 |
| 133 | RTEVTLETL | 12 | 9 |
| 754 | RSLTEGLVL | 12 | 10 |
| 429 | VFGYMSKFF | 10 | 11 |
| 436 | FFSGDLRDF | 10 | 12 |

| Start Position | amino acid sequence | Kd (nM) | SEQ ID NO |
|---|---|---|---|
| 524 | EWPSPAPSF | 99 | 13 |
| 241 | YMAMIQFAI | 421 | 14 |

TABLE 1b

HLA-A24 binding 10mer peptides derived from FOXM1

| Start Position | amino acid sequence | score | SEQ ID NO |
|---|---|---|---|
| 627 | SYSQeVGGPF | 140 | 15 |
| 240 | SYMAmIQFAI | 105 | 16 |
| 777 | SFPGlDEDPL | 30 | 17 |
| 453 | NFIFlCLSVL | 30 | 18 |
| 382 | QFPVnQSLVL | 30 | 19 |
| 483 | LFGEgFSPLL | 24 | 20 |
| 435 | KFFSgDLRDF | 20 | 21 |
| 396 | KVPLpLAASL | 14.4 | 22 |
| 325 | KPLDpGSPQL | 14.4 | 23 |
| 443 | DFGTpITSLF | 14 | 24 |
| 318 | LTLDqVFKPL | 12.096 | 25 |
| 713 | RLLSsEPLDL | 12 | 26 |
| 513 | RPIKvESPPL | 12 | 27 |
| 7 | RPLIlKRRRL | 12 | 28 |
| 376 | SYLVpIQFPV | 10.5 | 29 |
| 390 | VLQPsVKVPL | 10.08 | 30 |
| 238 | PYSYmAMIQF | 10 | 31 |

| Start Position | amino acid sequence | Kd (nM) | SEQ ID NO |
|---|---|---|---|
| 264 | TWIEDHFPYF | 20 | 32 |

Start position indicates the number of amino acid residue from the N-terminus of FOXM1

Binding score and dissociation constant [Kd (nM)] are derived from "BIMAS" and "NetMHC 3.0".

CTL Induction with the Predicted Peptides from FOXM1 Restricted with HLA-A*2402 and Establishment for CTL Lines Stimulated with FOXM1 Derived Peptides CTLs for those peptides derived from FOXM1 were generated according to the protocols as described in "Materials and Methods". Peptide specific CTL activity was determined by IFN-gamma ELISPOT assay (FIGS. 1a-g). It showed that the well numbers #1, #4 and #7 stimulated with FOXM1-A24-9-262 (SEQ ID NO: 2) (a), #7 with FOXM1-A24-9-351 (SEQ ID NO: 7) (b), #5 with FOXM1-A24-9-57 (SEQ ID NO: 8) (c), #3 with FOXM1-A24-10-240 (SEQ ID NO: 16) (d), #6 with FOXM1-A24-10-318 (SEQ ID NO: 25) (e), #4 with FOXM1-A24-10-390 (SEQ ID NO: 30) (f) and #5 with FOXM1-A24-10-238 (SEQ ID NO:31) (g) demonstrated potent IFN-gamma production as compared to the control wells. On the other hand, no potent IFN-gamma production could be detected by stimulation with other peptides shown in Tables 1a and 1b, despite those peptides had possible binding activity with HLA-A*2402. For example, typical negative data of CTL response stimulated with FOXM1-A24-9-316 (SEQ ID NO: 1) against peptide-pulsed target cells (h). As a result, it indicated that 7 peptides derived from FOXM1 were screened as the peptides that could induce potent CTLs.

Establishment of CTL Lines and Clones Against FOXM1 Derived Peptides

The cells that showed peptide specific CTL activity detected by IFN-gamma ELISPOT assay in the well numbers #4 with FOXM1-A24-9-262 (SEQ ID NO: 2) (a), #3 with FOXM1-A24-10-240 (SEQ ID NO: 16) (b), #6 with FOXM1-A24-10-318 (SEQ ID NO: 25) (c) and #5 with FOXM1-A24-10-238 (SEQ ID NO: 31) (d) were expanded and established CTL lines. CTL activity of those CTL lines was determined by IFN-gamma ELISA assay (FIGS. 2a-d). It showed that all CTL lines demonstrated potent IFN-gamma production against the target cells pulsed with corresponding peptide as compared to target cells without peptide pulse. Furthermore, CTL clones were established by limiting dilution from the CTL lines, and IFN-gamma production from CTL clones against target cells pulsed peptide was determined by IFN-gamma ELISA assay. Potent IFN-gamma production was determined from CTL clones stimulated with FOXM1-A24-9-262 (SEQ ID NO: 2) (a), FOXM1-A24-10-240 (SEQ ID NO: 16) (b) and FOXM1-A24-10-238 (SEQ ID NO: 31) (c) in FIG. 3.

Specific CTL Activity Against Target Cells Exogenously Expressing FOXM1 and HLA-A*2402

Figure 4:
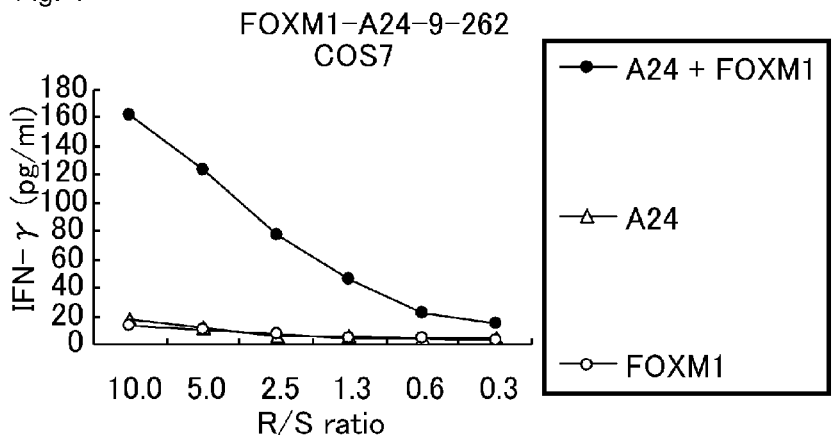
FIG. 4 depicts the line graphs showing specific CTL activity against the target cells that exogenously express FOXM1 and HLA-A*2402. COS7 cells transfected with HLA-A*2402 or the full length of FOXM1 gene were prepared as controls. The CTL clone established with the peptide of FOXM1-A24-9-262 (SEQ ID NO: 2) showed specific CTL activity against COS7 cells transfected with both FOXM1 and HLA-A*2402 (black lozenge). On the other hand, no significant specific CTL activity was detected against target cells expressing either HLA-A*2402 (white triangle) or FOXM1 (white circle).

The established CTL lines and clones raised against these peptides were examined for their ability to recognize target cells that endogenously express FOXM1 and HLA-A*2402 gene. Specific CTL activity against COS7 cells which transfected with both the full length of FOXM1 and HLA-A*2402 gene (a specific model for the target cells that exogenously express FOXM1 and HLA-A*2402 gene) was tested using the CTL lines and clones raised by corresponding peptide as the effector cells. COS7 cells transfected with either full length of FOXM1 genes or HLA-A*2402 were prepared as controls. In FIG. 4, the CTLs stimulated with FOXM1-A24-9-262 (SEQ ID NO: 2) showed potent CTL activity against COS7 cells expressing both FOXM1 and HLA-A*2402. On the other hand, no significant specific CTL activity was detected against the controls. Thus, these data clearly demonstrated that the peptide of FOXM1-A24-9-262 (SEQ ID NO: 2) was endogenously processed and expressed on the target cells with HLA-A*2402 molecule and were recognized by the CTLs. These results indicated that this peptide derived from FOXM1 may be available to apply the cancer vaccines for patients with FOXM1 expressing tumors.

Homology Analysis of Antigen Peptides

The CTLs stimulated with FOXM1-A24-9-262 (SEQ ID NO: 2), FOXM1-A24-9-351 (SEQ ID NO: 7), FOXM1-A24-9-57 (SEQ ID NO: 8), FOXM1-A24-10-240 (SEQ ID NO: 16), FOXM1-A24-10-318 (SEQ ID NO: 25), FOXM1-A24-10-390 (SEQ ID NO: 30) and FOXM1-A24-10-238 (SEQ ID NO: 31) showed significant and specific CTL activity. This result may be due to the fact that the sequences of FOXM1-A24-9-262 (SEQ ID NO: 2), FOXM1-A24-9-351 (SEQ ID NO: 7), FOXM1-A24-9-57 (SEQ ID NO: 8), FOXM1-A24-10-240 (SEQ ID NO: 16) FOXM1-A24-10-318 (SEQ ID NO: 25) FOXM1-A24-10-390 (SEQ ID NO: 30) and FOXM1-A24-10-238 (SEQ ID NO: 31) are homologous to peptides derived from other molecules that are known to sensitize the human immune system. To exclude this possibility, homology analyses were performed for these peptide sequences using as queries the BLAST algorithm (www.ncbi.nlm.nih.gov/blast/blast.cgi) which revealed no sequence with significant homology. The results of homology analyses indicate that the sequences of FOXM1-A24-9-262 (SEQ ID NO: 2), FOXM1-A24-9-351 (SEQ ID NO: 7), FOXM1-A24-9-57 (SEQ ID NO: 8), FOXM1-A24-10-240 (SEQ ID NO: 16) FOXM1-A24-10-318 (SEQ ID NO: 25) FOXM1-A24-10-390 (SEQ ID NO: 30) and FOXM1-A24-10-238 (SEQ ID NO: 31) are unique and thus, there is little possibility, to our best knowledge, that these molecules raise unintended immunologic response to some unrelated molecule.

In conclusion, novel HLA-A24 epitope peptides derived from FOXM1 were identified. Furthermore, it was demonstrated that epitope peptide of FOXM1 may be applicable for cancer immunotherapy.

INDUSTRIAL APPLICABILITY

The present invention provides new TAAs, particularly those derived from FOXM1 which induce potent and specific anti-tumor immune responses and have applicability to a wide array of cancer types. Such TAAs are useful as peptide vaccines against diseases associated with FOXM1, e.g., cancer, more particularly, AML, bladder cancer, breast cancer, cervical cancer, cholangiocellular carcinoma, CML, colorectal cancer, esophageal cancer, gastric cancer, gastric cancer diffuse-type, liver cancer, NSCLC, lymphoma, osteosarcoma, ovarian cancer, pancreatic cancer, prostate cancer, renal carcinoma, SCLC, soft tissue tumor and testicular tumor.

While the present invention is herein described in detail and with reference to specific embodiments thereof, it is to be understood that the foregoing description is exemplary and explanatory in nature and is intended to illustrate the present invention and its preferred embodiments. Through routine experimentation, one skilled in the art will readily recognize that various changes and modifications can be made therein without departing from the spirit and scope of the present invention, the metes and bounds of which are defined by the appended claims.

The invention claimed is:

1. An isolated peptide of less than 15 amino acids having cytotoxic T lymphocyte (CTL) inducibility, wherein the peptide comprises an amino acid sequence selected from the group consisting of:
   (i) an amino acid sequence selected from the group consisting of SEQ ID NOs: 2, 7, 8, 16, 25, 30 and 31; and
   (ii) an amino acid sequence selected from the group consisting of SEQ ID NOs: 2, 7, 8, 16, 25, 30 and 31, in which 1 or 2 amino acid(s) are substituted or added.

2. The isolated peptide of claim 1 which is a nonapeptide or decapeptide.

3. The peptide of claim 1 having one or both of the following characteristics:
   (a) the second amino acid from the N-terminus is selected from the group consisting of phenylalanine, tyrosine, methionine and tryptophan; and
   (b) the C-terminal amino acid is selected from the group consisting of phenylalanine, leucine, isoleucine, tryptophan and methionine.

4. A composition for inducing CTL, wherein the composition comprises the peptide of claim 1.

5. A pharmaceutical composition which comprises the peptide of claim 1.

6. A method for inducing an antigen-presenting cell (APC) with CTL inducibility, wherein the method comprises contacting an APC with the peptide of claim 1 in vitro, ex vivo or in vivo.

7. A method for inducing CTL comprising at least one of the following steps:
   (a) co-culturing a CD8-positive T cell with an APC, which presents on its surface a complex of an HLA antigen and the peptide of claim 1; and
   (b) co-culturing a CD8-positive T cell with an exosome, which presents on its surface a complex of an HLA antigen and the peptide of claim 1.

* * * * *